(12) United States Patent
Rosar

(10) Patent No.: US 6,223,083 B1
(45) Date of Patent: Apr. 24, 2001

(54) RECEIVER EMPLOYING DIGITAL FILTERING FOR USE WITH AN IMPLANTABLE MEDICAL DEVICE

(75) Inventor: George Rosar, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/293,261

(22) Filed: Apr. 16, 1999

(51) Int. Cl.⁷ ........................................... A61N 1/08
(52) U.S. Cl. .................. 607/60; 607/32; 128/903
(58) Field of Search ................ 607/27, 30–32, 607/60; 128/903

(56) References Cited

U.S. PATENT DOCUMENTS

| | | |
|---|---|---|
| 4,281,664 | 8/1981 | Duggan . |
| 4,375,817 | 3/1983 | Engle et al. . |
| 4,379,459 | 4/1983 | Stein . |
| 4,384,585 | 5/1983 | Zipes . |
| 4,476,868 | 10/1984 | Thompson . |
| 4,494,545 | 1/1985 | Slocum et al. . |
| 4,548,209 | 10/1985 | Wielders et al. . |
| 4,556,063 | 12/1985 | Thompson et al. . |
| 4,562,840 | 1/1986 | Batina et al. . |
| 4,571,589 | 2/1986 | Slocum et al. . |
| 4,577,633 | 3/1986 | Berkovitz et al. . |
| 4,587,970 | 5/1986 | Holley et al. . |
| 4,681,111 | 7/1987 | Silvian . |
| 4,693,253 | 9/1987 | Adams et al. . |
| 4,726,380 | 2/1988 | Vollmann et al. . |
| 4,757,816 | 7/1988 | Ryan et al. . |
| 4,821,723 | 4/1989 | Baker et al. . |
| 4,830,006 | 5/1989 | Haluska et al. . |
| 4,880,005 | 11/1989 | Pless et al. . |
| 4,944,299 | 7/1990 | Silvian . |
| 4,949,719 | 8/1990 | Pless et al. . |
| 4,949,730 | 8/1990 | Cobben et al. . |
| 5,058,581 | 10/1991 | Silvian . |
| 5,107,833 | 4/1992 | Barsness . |
| 5,127,404 | 7/1992 | Wyborny et al. . |
| 5,131,388 | 7/1992 | Pless . |
| 5,144,949 | 9/1992 | Olson . |
| 5,158,078 | 10/1992 | Bennett et al. . |
| 5,188,105 | 2/1993 | Keimel . |
| 5,199,428 | 4/1993 | Obel et al. . |
| 5,207,218 | 5/1993 | Carpentier et al. . |
| 5,241,961 | 9/1993 | Henry . |
| 5,264,843 | 11/1993 | Silvian . |

(List continued on next page.)

*Primary Examiner*—Jeffrey R. Jastrzab
(74) *Attorney, Agent, or Firm*—Thomas F. Woods; Harold R. Patton; Girma Wolde-Michael

(57) ABSTRACT

A receiving and filtering circuit includes an antenna, a demodulator circuit coupled to the antenna, and a digital median filter that removes high frequency content of a demodulated digital information signal to produce a filtered digital information signal corresponding to an analog data signal transmitted by a body implantable medical apparatus. The digital filter may include a multiple stage delay line coupled to a multiple tap selection device, a plurality of delay blocks coupled to a register, or a multiple stage delay line coupled to a voting unit. The voting unit produces a first binary output in response to a majority of delay line stages storing a first value, and produces a second binary output in response to a majority of delay line stages storing a second value. The digital filter may also comprise a digital signal processor. The digital filter may include a first filter block and a second filter block. The second filter block may be selectively activated or bypassed. The first filter block removes high frequency content of the digital information signal and the second filter block reduces high frequency noise at an edge of a data bit transition. A control circuit, coupled to the digital filter, provides for respective selection of data rate and frequency response characteristics of the digital filter. The digital filter may be implemented in a Field-Programmable Gate Array (FPGA) or an Application Specific Integrated Circuit (ASIC).

32 Claims, 19 Drawing Sheets

U.S. PATENT DOCUMENTS

| | | |
|---|---|---|
| 5,292,343 | 3/1994 | Blanchette et al. . |
| 5,300,093 | 4/1994 | Koestner et al. . |
| 5,312,453 | 5/1994 | Shelton et al. . |
| 5,314,430 | 5/1994 | Bardy . |
| 5,330,507 | 7/1994 | Schwartz . |
| 5,331,966 | 7/1994 | Bennet et al. . |
| 5,354,316 | 10/1994 | Keimel . |
| 5,383,912 | 1/1995 | Cox et al. . |
| 5,425,373 * | 6/1995 | Causey, III ................................ 607/27 |
| 5,447,519 | 9/1995 | Peterson . |
| 5,475,307 | 12/1995 | Silvian . |
| 5,545,186 | 8/1996 | Olson et al. . |
| 5,620,472 | 4/1997 | Rahbar . |
| 5,792,207 * | 8/1998 | Deitrich ................................ 607/32 |
| 5,999,857 * | 12/1999 | Weijand et al. ........................ 607/60 |

* cited by examiner

RECEIVER EMPLOYING DIGITAL FILTERING FOR USE WITH AN IMPLANTABLE MEDICAL DEVICE

FIELD OF THE INVENTION

The present invention relates generally to communication receivers adapted for use with an implantable medical device. More particularly, the present invention pertains to a receiver employing a digital filter for filtering demodulated data corresponding to data impressed on a carrier signal and transmitted from an implantable medical device.

BACKGROUND OF THE INVENTION

Various implantable medical devices have been developed that receive information from one or more physiologic sensors or transducers. A typical physiologic sensor transduces a measurable parameter of the human body, such as blood pressure, temperature or oxygen saturation for example, into corresponding electrical signals. At the appropriate time, the physiologic data acquired by an implantable medical device is uplinked to an external receiving system, such as a programmer, for storage and analysis.

In many implantable medical device applications, a radio frequency (RF) telemetry approach is used by which data acquired by an implantable medical device is impressed on a carrier signal and transmitted to an external receiving system during an data uplink procedure. A demodulation circuit is typically provided in the receiving system that recovers the physiologic information signal from a modulated signal received from the implantable medical device. An analog low pass filter is typically used to extract the physiologic information signal from the demodulated signal, which generally contains noise and exhibits other undesirable corruptive characteristics.

In many conventional receiving systems, noise is introduced into the RF signal channel from a number of traditional sources which corrupts the demodulated data signal. In addition, high frequency noise components are introduced into the demodulated data signal as a result of the demodulation process. Moreover, receiving systems that employ analog components generally experience problems that normally arise from processing of analog signals with relatively large signal swings and large bandwidths. Such problems include bit distortion due to low-to-high and high-to-low slew rate differences, failure to follow distortion (i.e., DC level shifts) caused by parasitic capacitances and charging of capacitors, failure to follow distortion caused by data in which there may be more positive data than negative data, and inter-symbol interference caused by tradeoffs in analog filter performance.

A traditional approach to addressing such signal corruption and processing problems involves the use of a programmable analog low pass filter, such as use of filters implemented in analog integrated circuits (IC's) and analog switches. Another traditional analog approach involves the use of a switched capacitor filter and an adjustable clock. Although analog low pass filtering provides for some degree of improvement in the extracted data signal, a successful analog low pass filtering circuit implementation is typically complex and requires a significant amount of printed circuit board space.

Further, a traditional analog low pass filtering approach typically involves a "custom" design, which is generally intolerant to changes in data rates and the frequency response of the filter. Such custom designs tend to be both expensive and limited in terms of the potential to use standardized, readily available, and relatively inexpensive electronic components. Still further, the use of analog components in a particular filter design is generally associated with increased power consumption, in contrast to a fully digital implementation. Increasing the power consumption requirements of the receiving system, including the filtering circuitry, may pose a significant problem in portable and small scale receiver applications.

Various implementations of RF telemetry systems directed for use with an implantable medical device are known in the art, examples of which may be found in the issued U.S. Patents listed in Table 1 below.

TABLE 1

| U.S. Pat. No. | Inventor(s) | Issue Date |
| --- | --- | --- |
| 4,281,664 | Duggan | August 4, 1981 |
| 4,494,545 | Slocum et al. | January 22, 1985 |
| 4,556,063 | Thompson et al. | December 3, 1985 |
| 4,562,840 | Batina et al. | January 7, 1986 |
| 4,571,589 | Slocum et al. | February 18, 1986 |
| 4,681,111 | Silvian | July 21, 1987 |
| 4,757,816 | Ryan et al. | July 19, 1988 |
| 4,949,299 | Silvian | July 31, 1990 |
| 5,058,581 | Silvian | October 22, 1991 |
| 5,107,833 | Barsness | April 28, 1992 |
| 5,127,404 | Wyborny at al. | July 7, 1992 |
| 5,241,961 | Henry | September 7, 1993 |
| 5,264,843 | Silvian | November 23, 1993 |
| 5,292,343 | Blanchette et al. | March 8, 1994 |
| 5,300,093 | Koestner et al. | April 5, 1994 |
| 5,312,453 | Shelton et al. | May 17, 1994 |
| 5,383,912 | Cox et al. | January 24, 1995 |
| 5,475,307 | Silvian | December 12, 1995 |
| 5,620,472 | Rahbar | April 15, 1997 |

The patents listed in Table 1 hereinabove are hereby incorporated by reference herein in their respective entireties. As those of ordinary skill in the art will appreciate readily upon reading the Summary of the Invention, the Detailed Description of Various Embodiments, and the claims set forth below, many of the devices and methods disclosed in the patents identified below and listed in Table 1 above may be modified advantageously by using the teachings of the present invention.

SUMMARY OF THE INVENTION

The present invention has certain objects. That is, various embodiments of the present invention provide solutions to one or more problems existing in the prior art with respect to telemetry receiving systems for use with implantable medical devices. Such problems associated with prior art receiving systems include, for example, those that arise from processing analog signals with relatively large signal swings and large bandwidths; an inability to utilize standardized, low-cost, and readily available electronic components, relatively large analog components that consume appreciable amounts of power and require a significant amount of printed circuit board space, and additional problems identified in the Background of the Invention.

Various embodiments of the present invention have the object of solving at least one of the foregoing problems. While some systems have been able to solve the general problem of filtering high frequency content from demodulated data produced by an implantable medical device, such approaches have generally resulted in implementations that increase noise, reduce frequency response and data rate adjustability, increase design and integration complexity, and increase the power consumed, and space occupied by, the filtering circuitry. It is therefore another object of the present invention to provide an improved apparatus and methodology for filtering demodulated RF data corresponding to data transmitted by an implantable medical device that fulfills at least one of the foregoing objects.

In comparison to known implementations of receiving system circuitry, various embodiments of the present invention may provide one or more of the following advantages: providing the opportunity to utilize standardized, low-cost, digital components in the filtering circuit design, eliminating all analog elements in the filtering circuitry, reducing the power and circuit board/chip space required to support the filtering circuitry, and increasing the adjustability of the filtering circuitry in terms of data rates and frequency response characteristics.

Some embodiments of the invention include one or more of the following features: a circuit for receiving and filtering data received from a body implantable medical apparatus, including an antenna, a demodulator circuit coupled to the antenna, and a digital filter that removes high frequency content of a demodulated digital information signal to produce a filtered digital information signal; a digital filter that comprises a multiple stage delay line coupled to a multiple tap selection device; a digital filter that includes a plurality of delay blocks and a register, each of the delay blocks having an input coupled to an output of the demodulator circuit and an output coupled to the register; a digital filter that comprises a multiple stage delay line and a voting unit, the voting unit producing a first binary output in response to a majority of delay line stages storing a first value, and the voting unit producing a second binary output in response to a majority of delay line stages storing a second value; a digital filter that comprises a digital signal processor; a digital filter that comprises a first block of filtering elements and a second block of filtering elements coupled to the first block of filtering elements, the second block of filtering elements selectably activated or bypassed in response to a selection signal; a digital filter that comprises a first filter block and a second filter block, the first filter block removing the high frequency content of the digital information signal and the second filter block reducing high frequency noise at an edge of a data bit transition of the digital information signal; a digital filter that operates as an accumulator buffer; a data rate control circuit, coupled to the digital filter, that provides for selection of a rate at that the digital filter operates; a digital filter that includes a plurality of delay blocks and a voting unit, each of the delay blocks including an input coupled to the demodulator circuit, and output coupled to the voting unit, and a clock input coupled to a clock circuit that produces a clock signal, further wherein varying a rate at which the digital filter operates is effected by the clock circuit varying a frequency of the clock signal, and further wherein varying a frequency response of the digital filter is effected by the clock circuit varying a frequency of the clock signal; a digital filter which is implemented in a Field-Programmable Gate Array (FPGA) or an Application Specific Integrated Circuit (ASIC); and a digital filter circuit that processes data received from any of a number of different implantable medical devices, including a pacemaker, a pacemaker/cardioverter/defibrillator (PCD), an oxygen sensing device, a nerve stimulator or a muscle stimulator.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
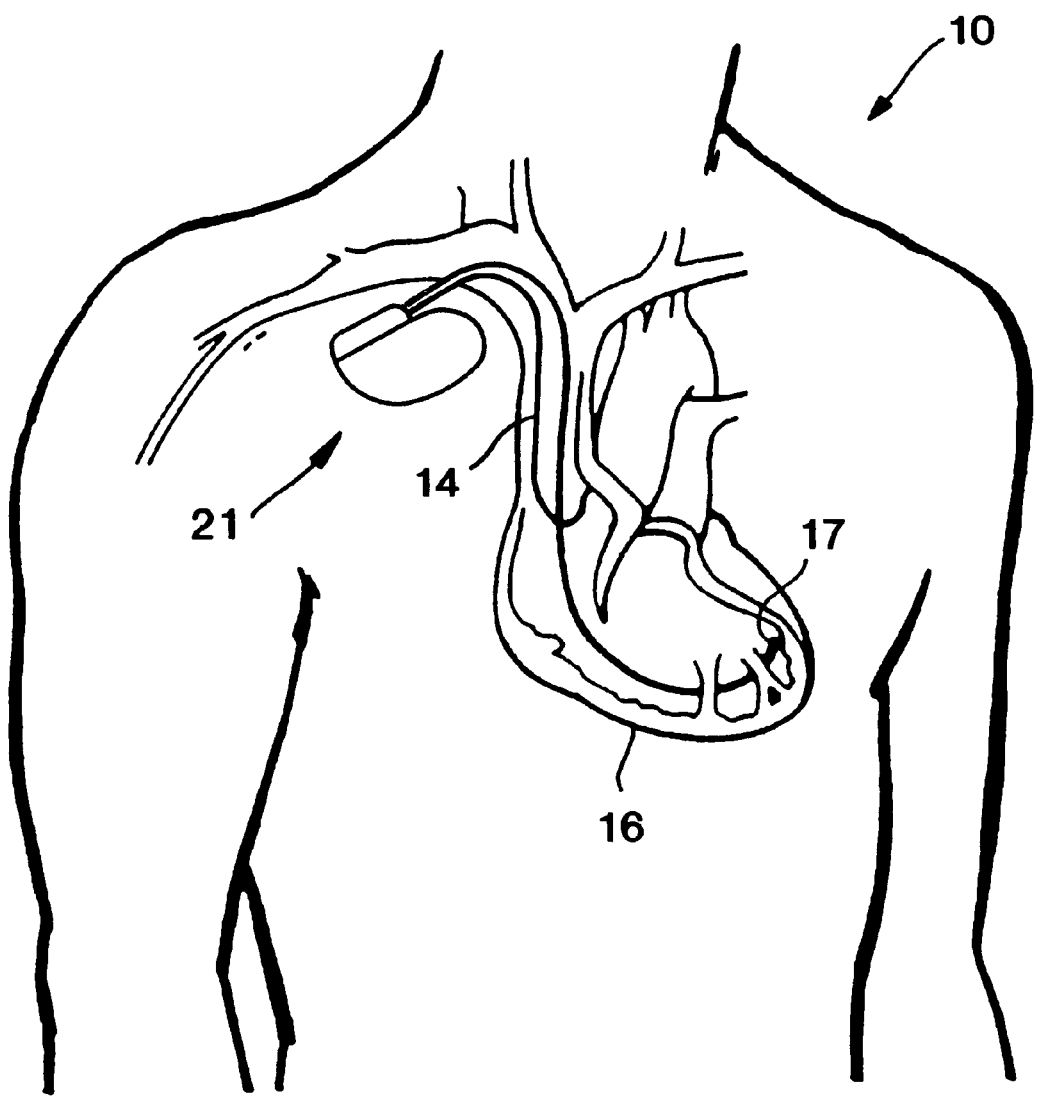
FIG. 1 shows an electrical medical device implanted in a human body that employs telemetry circuitry for transmitting modulated data for reception by a digital delay line receiver employing a digital filtering approach in accordance with an embodiment of the present invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Figure 3:
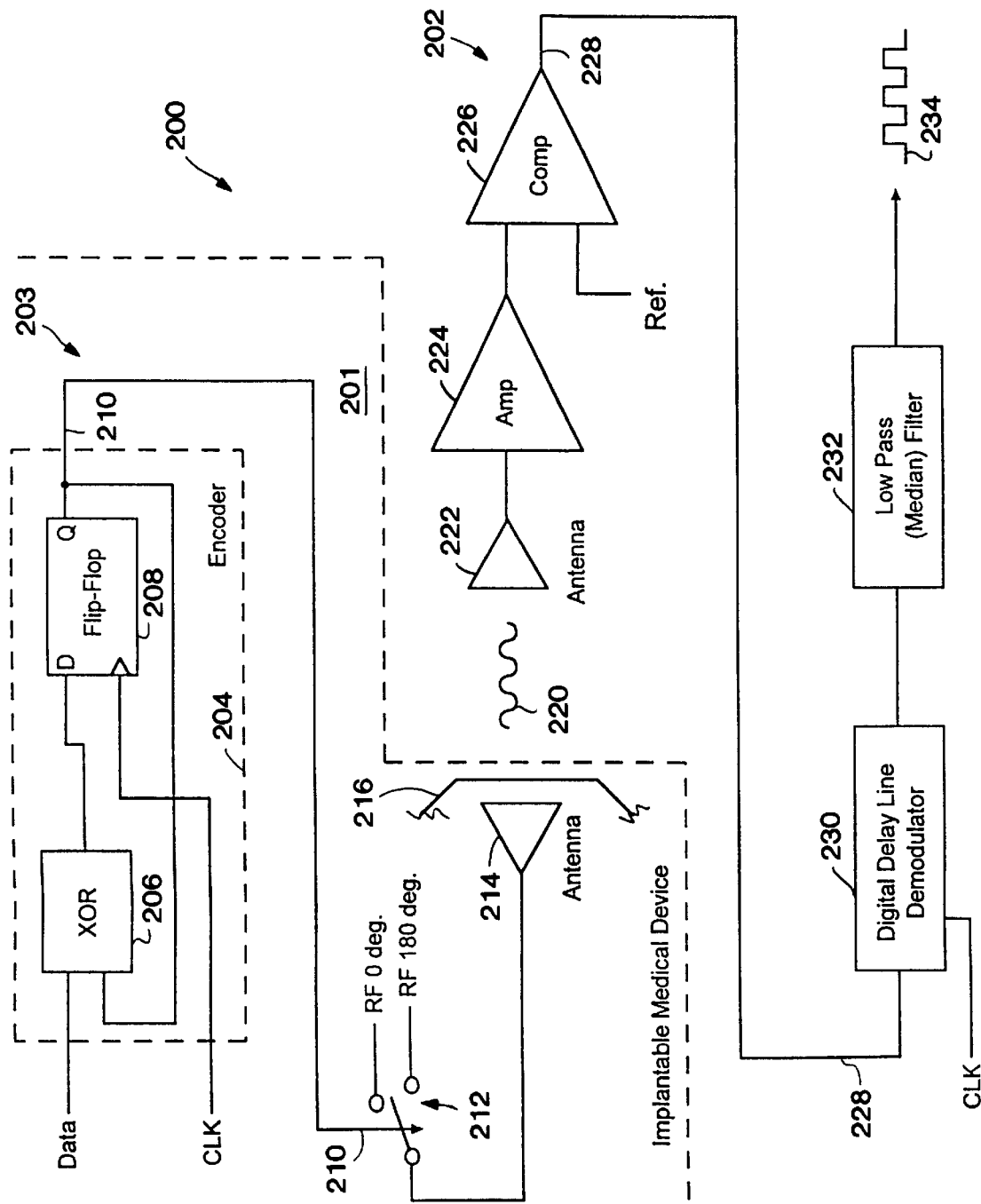
FIG. 3 shows a block diagram of a system for communicating data between an implantable medical device and a receiving/monitoring system.

FIG. 1 is a simplified schematic view of a medical device 21 implanted in a human body 10. A transducer assembly 17 is shown implanted in a human heart 16 and coupled to the medical device 21. The transducer assembly 17, as is shown in FIG. 3, includes two sensors 19, 20, each of which senses one or more physiologic parameters associated with the human heart 16. It is understood that transducer assembly 17 may include one sensor or more than two sensors. The lead 14 includes two conductors 13, 15. Each of the two sensors 19, 20 included within the transducer assembly 17 is coupled to one or both of the two conductors 13, 15 in either a series or parallel configuration. The two sensors 19, 20 of the transducer assembly 17 are selectively and alternately activated and deactivated in a manner appropriate for a particular physiologic sensor and monitoring application.

In the case where the implanted medical device 21 shown in FIG. 1 is a pacemaker, one of the two conductors 13, 15 of lead 14 is typically connected between the heart 16 from the implantable medical device 21. The lead 14, which typically includes a tine electrode, senses electrical signals attendant to the depolarization and re-polarization of the heart 16 and transmits pacing pulses for causing depolarization of cardiac tissue in the vicinity of the distal ends thereof. The medical device 21 may be an implantable cardiac pacemaker, such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties.

The implantable medical device 21 may also be a pacemaker/cardioverter/defibrillator (PCD), one embodiment of which is further described below. The present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties.

Alternatively, the medical device 21 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al., all of which are hereby incorporated herein by reference in their respective entireties. The present invention is believed to find wide application to any form of implantable electrical device which utilizes a radio frequency (RF) telemetry approach for communicating information from an implantable medical device to an external receiver/monitoring system, such as a programmer.

In general, the implantable medical device 21 shown in FIG. 1 includes a hermetically-sealed enclosure that may include various elements, such as an electrochemical cell (e.g., a lithium battery), circuitry that controls device operations and records arrhythmic EGM episodes, telemetry transceiver antenna and circuit that receives downlinked telemetry commands from and transmits stored data in a telemetry uplink to an external programmer, in addition to other elements.

Figure 2A:
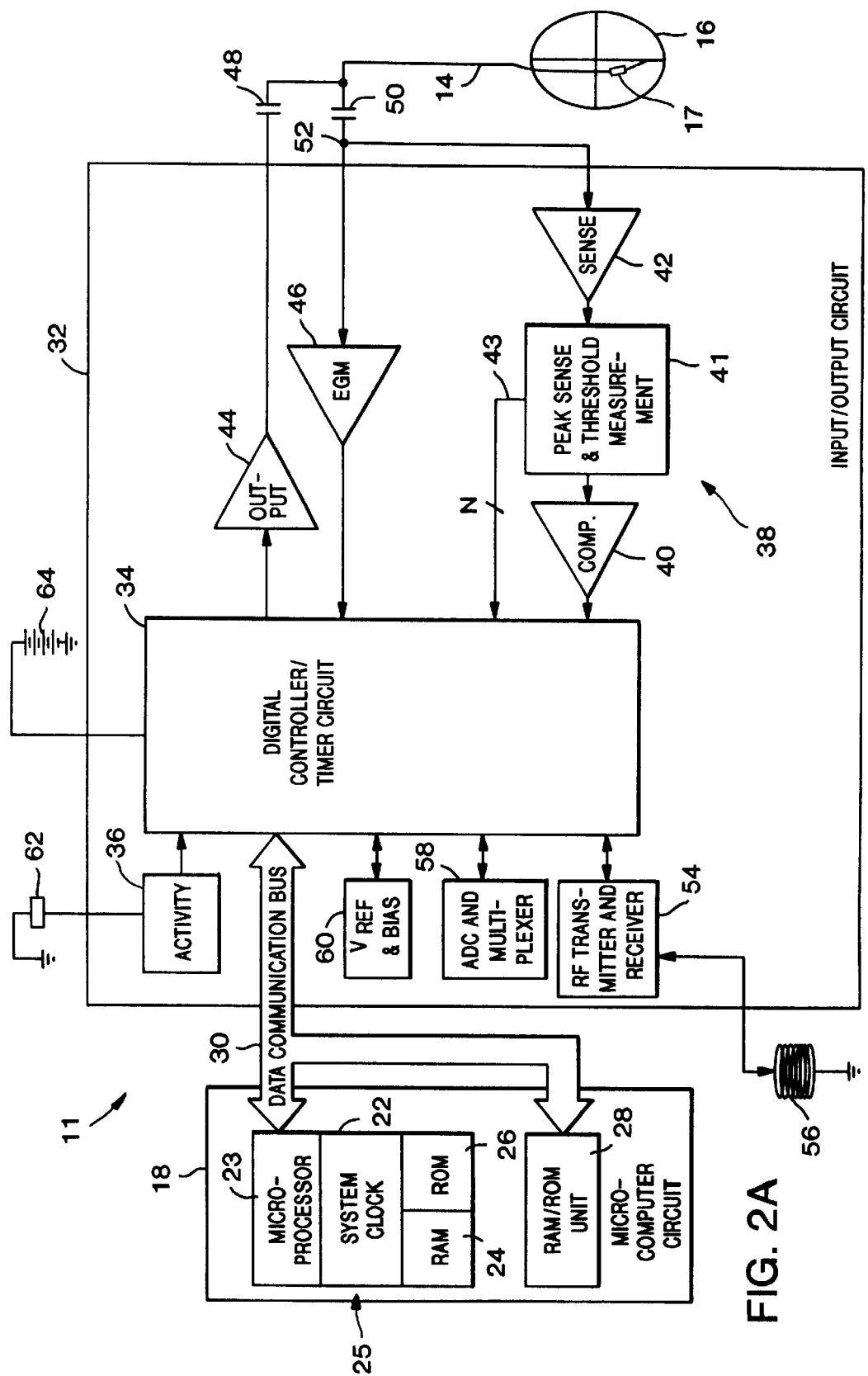
FIG. 2A shows an implantable pacemaker device employing telemetry circuitry for transmitting modulated data for reception by a digital delay line receiver employing a digital filtering approach in accordance with an embodiment of the present invention.

FIG. 2A is a block diagram illustrating various components of a pacemaker 11 which represents one of many implantable medical devices that may advantageously communicate modulated IMD data to a receiver circuit which employs a digital median filter in accordance with the present invention. In one embodiment, the pacemaker 11 is programmable by means of an external programming unit (not shown). One such programmer suitable for the purposes of the present invention is the commercially available Medtronic Model 9790 programmer. The programmer is a microprocessor-based device which provides a series of encoded signals to pacemaker 11 by means of a programming head which transmits radio frequency (RF) encoded signals to pacemaker 11 according to a telemetry system such as that described in U.S. Pat. No. 5,312,453 to Shelton et al., the disclosure of which is hereby incorporated by reference herein in its entirety. It is to be understood, however, that the programming methodology disclosed in the Wyborny et al. patent is identified herein for illustrative purposes only and that any programming methodology may be employed so long as the desired information is transmitted to and from the pacemaker 11. One of skill in the art may choose from any of a number of available programming techniques to accomplish this task.

Pacemaker 11, illustratively shown in FIG. 2A, is electrically coupled to the patient's heart 16 by lead 14. Lead 14, which includes two conductors, is coupled to a node 52 in the circuitry of pacemaker 11 through input capacitor 50. In the presently disclosed embodiment, an activity sensor 62 provides a sensor output to a processing/amplifying activity circuit 36 of input/output circuit 32. InpuVoutput circuit 32 also contains circuits for interfacing with heart 16, antenna 56, and circuits 44 for application of stimulating pulses to heart 16 to moderate its rate under control of software-implemented algorithms in microcomputer unit 18.

Microcomputer unit 18 comprises on-board circuit 25 which includes microprocessor 20, system clock 22, and on-board RAM 24 and ROM 26. In this illustrative embodiment, off-board circuit 28 comprises a RAM/ROM unit. On-board circuit 25 and off-board circuit 28 are each coupled by a data communication bus 30 to digital controller/timer circuit 34.

The electrical components shown in FIG. 2A are powered by an appropriate implantable battery power source 64 in accordance with common practice in the art. For purposes of clarity, the coupling of battery power to the various components of pacemaker 11 is not shown in the figures.

Antenna 56 is connected to input/output circuit 32 to permit uplink/downlink telemetry through RF transmitter and receiver unit 54. Unit 54 may correspond to the telemetry and program logic disclosed in U.S. Pat. No. 4,556,063 issued to Thompson et al., hereby incorporated by reference herein in its entirety, or to that disclosed in the above-referenced Wyborny et al. patent.

Voltage reference ($V_{REF}$) and bias circuit 60 generates a stable voltage reference and bias current for the analog circuits of input/output circuit 32. Analog-to-digital converter (ADC) and multiplexer unit 58 digitizes analog signals and voltages to provide "real-time" telemetry intracardiac signals and battery end-of-life (EOL) replacement functions.

Operating commands for controlling the timing of pacemaker 11 are coupled by data bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sensing circuitry 38, including sense amplifier 42, peak sense and threshold measurement unit 41, and comparator/threshold detector 40.

Sense amplifier 42 amplifies sensed electrocardiac signals and provides an amplified signal to peak sense and threshold measurement circuitry 41. Circuitry 41, in turn, provides an indication of peak sensed voltages and measured sense amplifier threshold voltages on path 43 to digital controller/timer circuit 34. An amplified sense amplifier signal is then provided to comparator/threshold detector 40. Sense amplifier 42 may correspond to that disclosed in U.S. Pat. No. 4,379,459 to Stein, which is hereby incorporated by reference herein in its entirety.

Circuit 34 is further preferably coupled to electrogram (EGM) amplifier 46 for receiving amplified and processed signals sensed by an electrode disposed on lead 14. The electrogram signal provided by EGM amplifier 46 is employed when the implanted device is being interrogated by an external programmer (not shown) to transmit by uplink telemetry a representation of an analog electrogram of the patient's electrical heart activity. Such functionality is, for example, shown in previously referenced U.S. Pat. No. 4,556,063.

Output pulse generator 44 provides pacing stimuli to the patient's heart 16 through coupling capacitor 48 in response to a pacing trigger signal provided by digital controller/timer circuit 34. For example, each time the escape interval times out, an externally transmitted pacing command is received, or such commands are received in response to other stored commands as is well known in pacing art. Output amplifier 44, for example, may correspond generally to the output amplifier disclosed in U.S. Pat. No. 4,476,868 to Thompson, also incorporated by reference herein in its entirety.

Figure 2B:
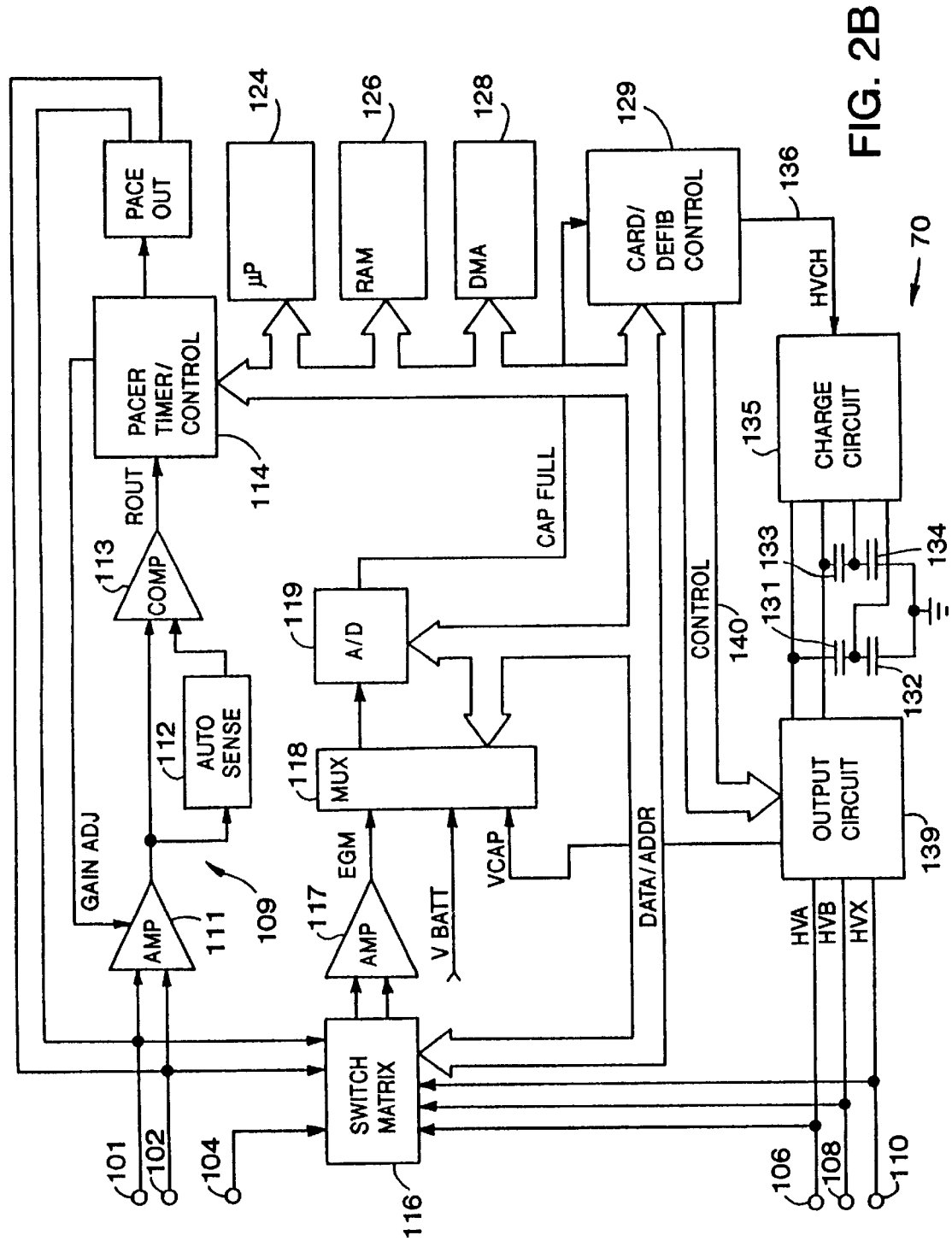
FIG. 2B shows one illustrative embodiment of a pacemaker/cardioverter/defibrillator unit employing telemetry circuitry for transmitting modulated data for reception by a digital delay line receiver employing a digital filtering approach in accordance with another embodiment of the present invention.

FIG. 2B is a functional schematic diagram from U.S. Pat. No. 5,447,519 to Peterson which shows an implantable pacemaker/cardioverter/defibrillator (PCD) 70 which represents another one of many implantable medical devices that may communicate modulated IMD data to a receiver circuit which employs a digital median filter in accordance with the present invention. U.S. Pat. No. 5,447,519 is incorporated by reference herein in its entirety.

It is understood that this diagram is an illustration of an exemplary type of device in which the invention may find application, and is not intended to limit the scope of the present invention. Other implantable medical devices, such as those described previously, having functional organizations wherein the present invention may be useful, may also be modified to incorporate modulation circuitry for communicating modulated IMD data to a receiver circuit which employs a digital median filter in accordance with the present invention. For example, the present invention is also believed to be useful in conjunction with implantable pacemakers/cardioverters/defibrillators as disclosed in U.S. Pat. No. 4,548,209 to Wielders, et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their respective entireties.

The PCD device 70 is provided with six electrodes 101, 102, 104, 106, 108, and 110. For example, electrodes 101 and 102 may be a pair of closely-spaced electrodes located in the ventricle. Electrode 104 may correspond to a remote, indifferent electrode located on the housing of the implantable PCD 70. Electrodes 106, 108, and 110 may correspond to large surface area defibrillation electrodes located on device leads or to epicardial electrodes.

Electrodes 101 and 102 are connected to detector circuit 109 which includes band pass filtered amplifier 111, auto-threshold circuit 112, which provides an adjustable sensing threshold, and comparator 113. A signal is generated by the comparator 113 whenever the signal sensed between electrodes 101 and 102 exceeds the sensing threshold defined by auto-threshold circuit 112. Further, the gain of amplifier 111 is adjusted by pacer timing and control circuitry 114. The sense signal, for example, is used to set the timing windows and to align successive waveshape data for morphology detection purposes. For example, the sense event signal may be routed through the pacer/timer control circuit 114 on data bus 115 to processor 124 and may act as an interrupt for processor 124 such that a particular routine of operations is commenced by processor 124.

Switch matrix 116 is used to select available electrodes under the control of processor 124 via data/address bus 115, such that the selection includes two electrodes employed as a far field electrode pair in conjunction with a tachycardia/fibrillation discrimination function. Far field EGM signals from the selected electrodes are passed through band pass amplifier 117 and into multiplexer 118, where they are converted to multi-bit digital data signals by A/D converter 119 for storage in random access memory 126 under the control of direct memory address circuitry 128.

The processor 124 may perform various morphology detection functions. For example, such detection functions may be indicative of tachycardia or fibrillation, or various other functions may be performed as set out in numerous references including any of the references incorporated herein by reference and others with regard to implantable PCDs.

The remainder of the device 70 of FIG. 2B is dedicated to the provision of cardiac pacing, cardioversion, and defibrillation therapies. The pacer timing/control circuit 114 includes programmable digital counters that control the basic timing intervals associated with cardiac pacing. Further, under control of processor 124, pacer timing/control circuit 114 also determines the amplitude of such cardiac pacing pulses.

In the event that a tachyarrhythmia is detected, and an anti-tachyarrhythmia pacing therapy is desired, appropriate timing intervals for controlling generation of pacing therapies are loaded from processor 124 into pacer timing and control circuitry 114. Similarly, in the event that generation of a cardioversion or defibrillation pulse is required, processor 124 employs the timing and control circuitry 114 to control timing of such cardioversion and defibrillation pulses.

In response to detection of fibrillation or a tachycardia requiring a cardioversion pulse, processor 124 activates cardioversion/defibrillation control circuitry 129, which initiates charging of the high voltage capacitors 131–134 via charging circuit 135 under the control of high voltage charging line 136. Thereafter, delivery and timing of the defibrillation or cardioversion pulse is controlled by pacer timing/control circuitry 114. One embodiment of an appropriate system for delivering and synchronizing cardioversion and defibrillation pulses, and controlling the timing functions related thereto, is disclosed in greater detail in U.S. Pat. No. 5,188,105 to Keimel, which is incorporated herein by reference in its entirety.

Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,374,817 to Engle et al., all of which are incorporated herein by reference in their respective entireties. Further, known circuitry for controlling the timing and generation of anti-tachycardia pacing pulses is described in U.S. Pat. No. 4,577,633 to Berkovitz et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their respective entireties.

Many implantable medical devices, such as those disclosed herein, utilize RF telemetry circuitry for modulating IMD data and uplinking such modulated IMD data to an external receiver/monitoring system, such as a programmer. It is considered desirable that the circuitry receiving the modulated uplinked IMD data provide for wide frequency tolerances in the IMD data. Improved signal-to-noise ratio performance is also considered desirable in order to provide for a high degree of IMD data integrity and transmission/reception reliability. It is also desirable to reduce the cost and size of the IMD data receiving circuitry, such as by exploiting standardized, low cost digital components. Reducing the power requirements of the IMD data receiving circuitry is also considered desirable.

A digital delay line receiver employing a digital filtering approach consistent with the principles of the present invention provides for all of the above-described advantages, as well as other advantages discussed hereinbelow. A digital delay line receiver having a digital filtering capability of the present invention further provides for the production of a substantially noise-free demodulated IMD data signal which is a highly accurate digital representation of the information signal content contained in the modulated analog IMD data signal uplinked from an implantable medical device.

FIG. 3 shows a block diagram of a system 200 for communicating data between an implantable medical device 201 and a receiving/monitoring system 202. The components of system 200 shown in FIG. 3 are operative during uplinking of data transmitted by IMD 201 and received by receiver/monitoring system 202. In accordance with this embodiment, IMD 201 includes an encoder 204 which encodes physiologic and other data acquired by, or otherwise produced by, IMD 201, such as data acquired by use of one or more physiologic sensors disposed on a lead which extends from IMD 201 into a patient's heart.

The encoded data generated by encoder 204 is further processed by modulation circuitry 212. A modulated RF data signal 220 is transmitted through the protective housing of IMD 201, often referred to as a can 216, by use of an antenna 214. The modulated data signal 220 propagates or is magnetically coupled via body tissue and air, and is received by an antenna 222 of the receiving/monitoring system 202. The received analog data signal 220 is amplified by amplifier 224 and converted to digital form by a comparator 226. The digitized data signal produced at output 228 of comparator 226 is applied to an input of a digital delay line demodulator 230.

Demodulator 230, in accordance with the principles of the present invention, recovers the information content (e.g., physiologic data) of the modulated data signal 220 in the digital domain. In accordance with the embodiment shown in FIG. 3, the digital information signal recovered by demodulator 230 is applied to an input of a digital low pass filter 232 which filters the recovered digital information signal by removing high frequency content therefrom which results from upstream signal processing and from the demodulation process. The extracted information signal, which is represented as a binary bit stream 234, is provided at the output of digital low pass filter 232.

A significant advantage realized through implementing a digital demodulation and filtering approach consistent with the principles of the present invention concerns the opportunity to use standardized, low-cost, and readily available digital components within the receiver channel circuitry. By way of example, digital delay line demodulator 230 and digital low pass filter 232 may be embodied in an FPGA, a digital portion of an ASIC, or through use of other standard digital components.

Use of such standardized digital components provides a number of performance advantages over traditional discrete component implementations, such as implementations that employ analog or mixed analog/digital components. Such performance advantages include improved signal-to-noise ratio performance which starts to approach theoretical limits (i.e., reduces implementation errors to nearly zero). Another performance advantage concerns wide data and carrier frequency tolerances, which allows for generous frequency variations in the data signal produced by the implantable medical device.

Another advantage realized through employment of a demodulator and filtering approach consistent with the principles of the present invention concerns the elimination of external components and circuitry associated with traditional implementations, such as by implementing the demodulation and filtering circuitry in an FPGA or ASIC. Employing a demodulation/filtering approach of the present invention provides the additional advantage of significantly simplifying the design of the receiver section of the receiver/monitoring system 202, as can be appreciated by a review of the circuitry depicted in FIG. 3.

In particular, and as is shown in FIG. 3, processing of a received analog data signal 220 may be converted to a digital/binary form through use of amplifier 224 and comparator 226, both of which are of a relatively simple design. Those skilled in the art will appreciate that the aforementioned advantages and those advantages discussed hereinbelow provide for a demodulation and filtering approach which advantageously increases processing efficiency, reduces circuit size, and reduces the complexity of implementation.

With further reference to FIG. 3, encoder 204 preferably employs a differential coding approach through use of an exclusive OR (XOR) gate 206 and a D flip-flop 208. The coded input data, which typically represents physiologic data acquired by one or more physiologic sensors coupled to the implantable medical device 201, is used to modulate an RF carrier signal through use of a modulator 212.

In this embodiment, modulator 212 is modeled as a single pole, double throw switch which switches between in-phase (0°) and out of phase (180°) terminals. It is noted that the carrier signal produced by modulator 212 may have a frequency of 175 kilohertz (KHz) which may or may not be synchronous with respect to data input to encoder 204. In one embodiment, modulator 212 produces a differential coded data signal. The modulated information signal produced by modulator 212 is communicated to antenna 214 which, in turn, transmits the modulated signal through a wall of IMD housing 216 for subsequent reception by receiver/monitoring system 202. Examples of circuitry and techniques for producing a modulated IMD data signal of a type readily accommodated by a demodulation and filtering approach consistent with the principles of the present invention are disclosed in one or more of the U.S. Patents listed in Table 1 hereinabove.

Figure 4:
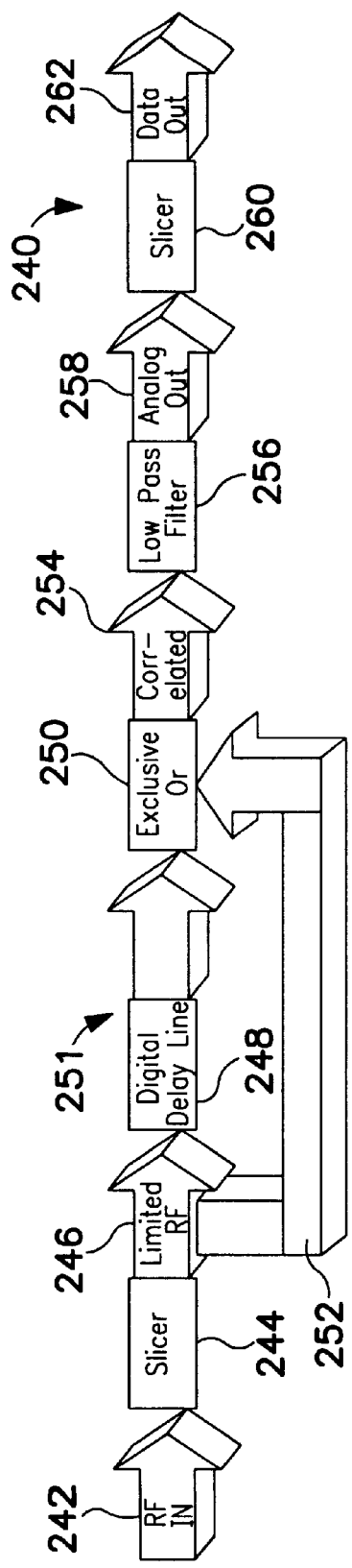
FIG. 4 shows a block diagram of a demodulation and filtering apparatus that digitally demodulates a modulated radio frequency (RF) signal transmitted by an implantable medical device and extracts an information signal therefrom using an analog filter in accordance with an embodiment of the present invention.

FIG. 4 shows a block diagram of a digital delay line receiver 240 in accordance with an embodiment of the present invention. In this embodiment, receiver 240 includes, among other components, a digital delay line 248, and XOR gate 250, a conductor 252, and an analog low pass filter 256. Receiver 240 receives a modulated RF signal 242 transmitted by an implantable medical device, such as IMD 201 depicted in FIG. 3. The received modulated signal 242 is input to a slicer 244 which converts the analog modulated signal 242 into a corresponding binary signal.

The binary modulated signal produced by slicer 244 is then processed by a limiter 246, which produces an amplitude limited binary modulated signal at its output. Those skilled in the art will appreciate that processing the binary modulated signal by use of limiter 246 so as to produce an amplitude limited (e.g., clipped) binary modulated signal advantageously eliminates the need to subject the signal to equalization and/or automatic gain control processing. Employing limiter 246 for purposes of producing an amplitude limited binary modulated signal in this manner provides for reduced circuit/signal processing complexity and cost.

It is understood that a mismatch between transmitting and receiving antenna quality factors (Q's) typically results in corruption of the transferred signal in a non-controlled manner. For example, the Q of the transmitting antenna provided in the implantable medical device may have a Q of 5, whereas the receiving antenna at the receiver/monitoring system location may have a Q of 1. Limiter 246 is employed to advantageously eliminate amplitude variations in the binary modulated signal within the RF signal channel. In this regard, bit-to-bit amplitude variations are removed in the binary modulated signal by limiter 246. The binary signal processed by limiter 246 is then input to digital delay line 248 of demodulator 251.

It is noted that a traditional IMD data demodulation approach generally requires multiple transformations of the data during various steps in the demodulation process, typically from an analog form to a digital form (A-to-D), from a digital form to an analog form (D-to-A), and back to a digital form (A-to-D). Those skilled in the art readily appreciate the difficulty of selecting and maintaining an appropriate threshold associated with the conversion of data from an analog form to a digital form within a receiver system environment. Employing a demodulation approach consistent with the principles of the present invention advantageously eliminates the need to perform such multiple transformations in the embodiments shown in FIGS. 4 and 5, eliminates problems associated with establishing/maintaining A-to-D conversion thresholds, and reduces problems with hysteresis, as all demodulation processes occur in the digital domain. By way of example, demodulation of IMD data may be accomplished entirely within an FPGA or an ASIC device.

Demodulator 251, as will be described in greater detail hereinbelow, demodulates the modulated binary signal received from limiter 240. The binary signal processed by digital delay line 248 of demodulator 251 is communicated to a first input of XOR gate 250. A delay path is provided between an input of limiter 246 and a second input of XOR gate 250 via conductor 252. The delay rate associated with delay path 252 may be generally characterized by the equation $N(T/2)$, where T represents the period of the binary signal and N is an integer (e.g., 1, 2, 3, . . . , M). The delay rate, for example, may be one full bit time, but may be less than (e.g., ½) or greater than (e.g., 3⁄2) one full bit time. The non-delayed limited binary signal produced at the output of digital delay line 248 and the delayed limited binary signal transmitted along delay path 252 are processed by XOR gate 250 to produce a correlated binary signal 254 at an output of XOR gate 250.

In this regard, receiver 240 may be viewed as a phase detector which is used to detect the coherent information between data bits. A fixed reference or an adaptive reference may be used in slicer 244, and the entire demodulation system can be performed digitally downstream of limiter 246.

A correlated binary signal 254 is produced at the output of XOR gate 250, which is applied to the input of an analog low pass filter 256. In this configuration, filter 256 represents a conventional analog low pass filter that removes undesirable high frequency signal content typically above the data frequency. The analog filtered signal produced at the output of low pass filter 256 is provided at the input of a slicer 260 which, in turn, produces a digital bit stream of binary data 262 corresponding to the information content impressed in the modulated RF data signal 242 received by receiver 240.

Figure 5:
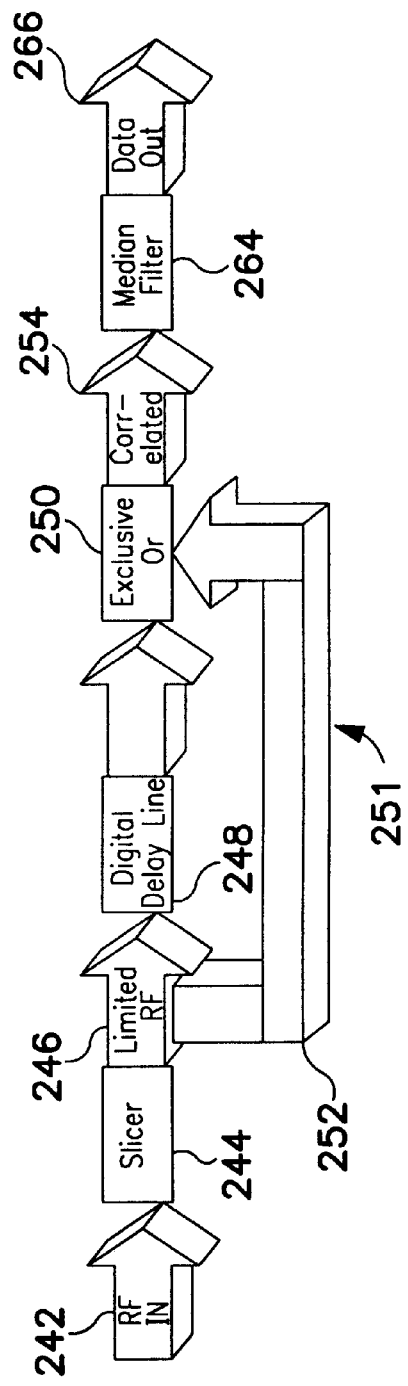
FIG. 5 shows a block diagram of a demodulation and filtering apparatus that digitally demodulates a modulated RF signal transmitted by an implantable medical device and extracts an information signal therefrom using a digital filter in accordance with an embodiment of the present invention.

In accordance with another embodiment of the present invention, and with reference to FIG. 5, low pass filtering of the correlated binary signal 254 produced at the output of XOR gate 250 may be accomplished by use of a digital filter 264, which provides for a fully digital telemetry demodulation and filtering approach. Digital filter 264 shown in FIG. 5 effectively replaces analog low pass filter 256 and slicer 260 of the receiver implementation depicted in FIG. 4. As will be described in greater detail hereinbelow, digital filter 264 is a non-linear filter within which, during each sample period, an array of binary values is sorted, and an output value of 1 or 0 is returned depending on whether the majority of values are 1's or 0's. Median filter 264, in this regard, may be termed a median smoothing filter which removes undesirable high frequency content from the demodulated signal, typically above the data frequency.

Figures 6A, 6B:
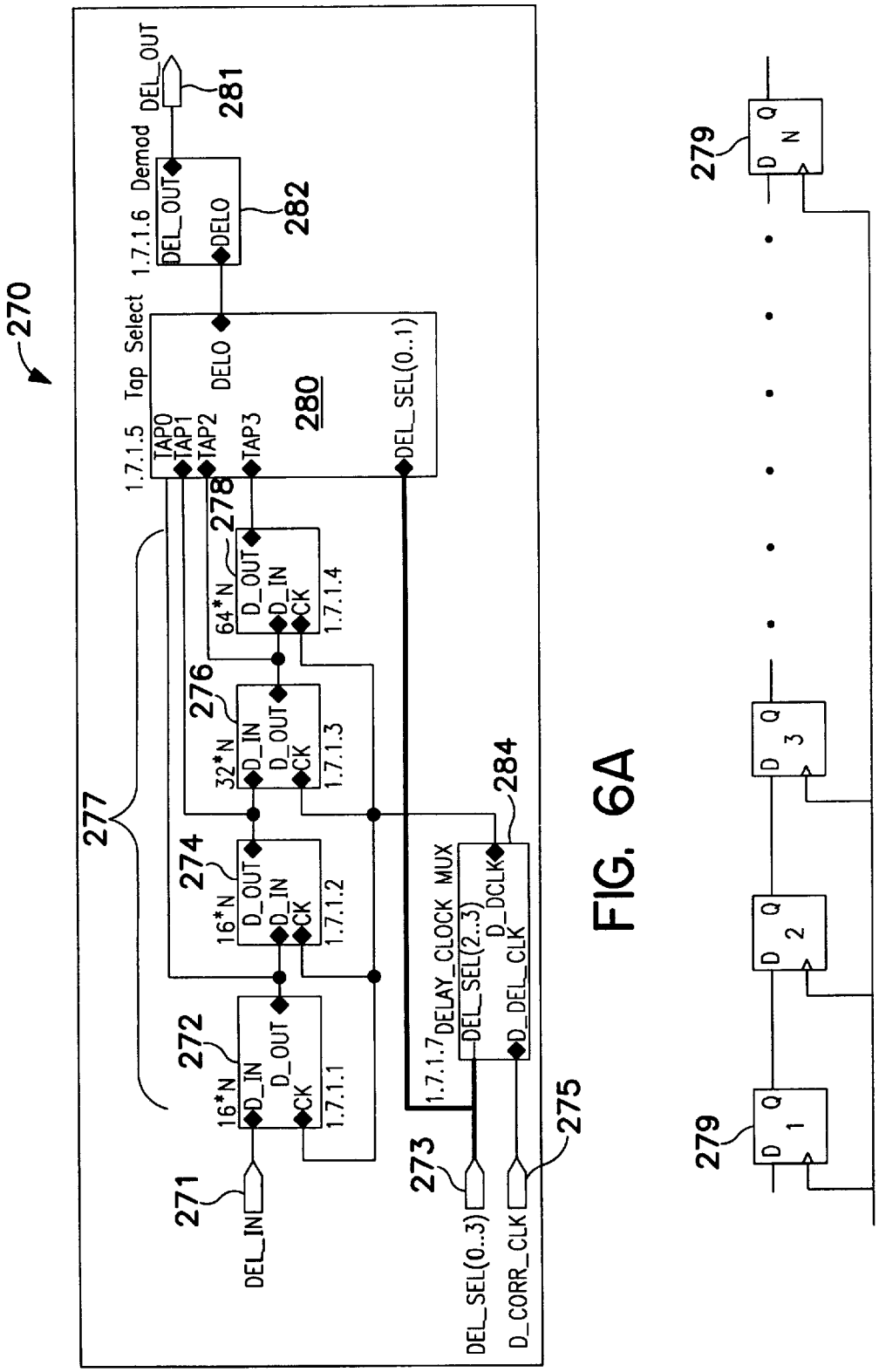
FIG. 6A is a block diagram of a digital delay line demodulator circuit in accordance with an embodiment of the present invention.
FIG. 6B is a schematic depiction of various components of a delay block of the type shown in FIG. 6A.

FIG. 6A is a detailed block diagram of a digital delay line demodulator 270 in accordance with an embodiment of the present invention. According to this embodiment, demodulator 270 is employed to demodulate a differential bi-phase-shift-keyed data signal produced by an implantable medical device. Demodulator 270 includes a number of delay blocks 272, 274, 276, and 278 to define a delay line block 277. In one configuration, delay line block 277 includes two 16-stage synchronous shift registers 272, 274, a synchronous 32-stage shift register 276, and a 64-stage shift register 278.

Each of the delay blocks 272, 274, 276, 278 includes a data input, a data output, and a clock input. In one embodiment, as is shown in FIG. 6B, each of the delay blocks, such as delay block 272, includes a number of delay elements 279, in this case D flip-flops. In the configuration shown in FIG. 6A, an input data signal processed by demodulator 270 will be delayed by 16, 32, 64, or 128 time slots. The sample rate of delay line block 277 is determined by a delay clock multiplexer 284 which provides for a multiplicity of clock rates. As such, the data rate through demodulator 270 may be selectively adjusted by appropriately adjusting the clock rate input to delay clock multiplexer 284.

With further reference to FIG. 6A, a modulated digital signal 271, identified as signal DEL_IN, is applied to the data input of delay element 272. Input signal 271 represents a signal that is correlated with a time delayed sampled version of itself. Input signal 271 is processed through delay line block 277 and subsequently demodulated in demodulation block 282. It is noted that input signal 271 has any amplitude variation removed therefrom, typically through use of an upstream comparator, such as comparator 226 shown in FIG. 3 or through digital signal processing (DSP) techniques. Signal 273, identified as signal DEL_SEL [0 . . . 3], is used to determine which tap(s) of tap select device 280 is selected, as well as the clock which controls the rate of delay line demodulator 270.

Signal 275, identified as signal D_CORR_CLK, provides the delay line clock multiplexer 284 with the highest available clock frequency used for the delay line demodulator 270. By way of example, the highest available clock frequency used for the delay line demodulator 270 may be 11.2 MHz. The clock frequency may be divided down by one of many dividers to provide for selection of a desired correlator clock rate. An integer ratio of the highest available clock rate, for example, may provide the basis for selecting the correlator clock rate, although fractional dividers may also be employed. In one embodiment, the correlator clock rate, and thus the data rate, is divisible by dividers of $2^N$, where N is an integer. For example, the frequency of the correlator clock may be 1.4 MHz, which may be achieved using the integer 8 (i.e., $2^3$) as the clock frequency divider. Alternatively, a frequency synthesizer may be employed to control the correlator clock rate, and thus the data rate, using known techniques.

The output signal 281, identified as signal DEL_OUT, represents a demodulated digital signal produced at the output of delay line demodulator 270. The output digital signal 281 typically contains high frequency noise and other undesirable high frequency content, and is further processed by one or more low pass filters.

Figure 7A:
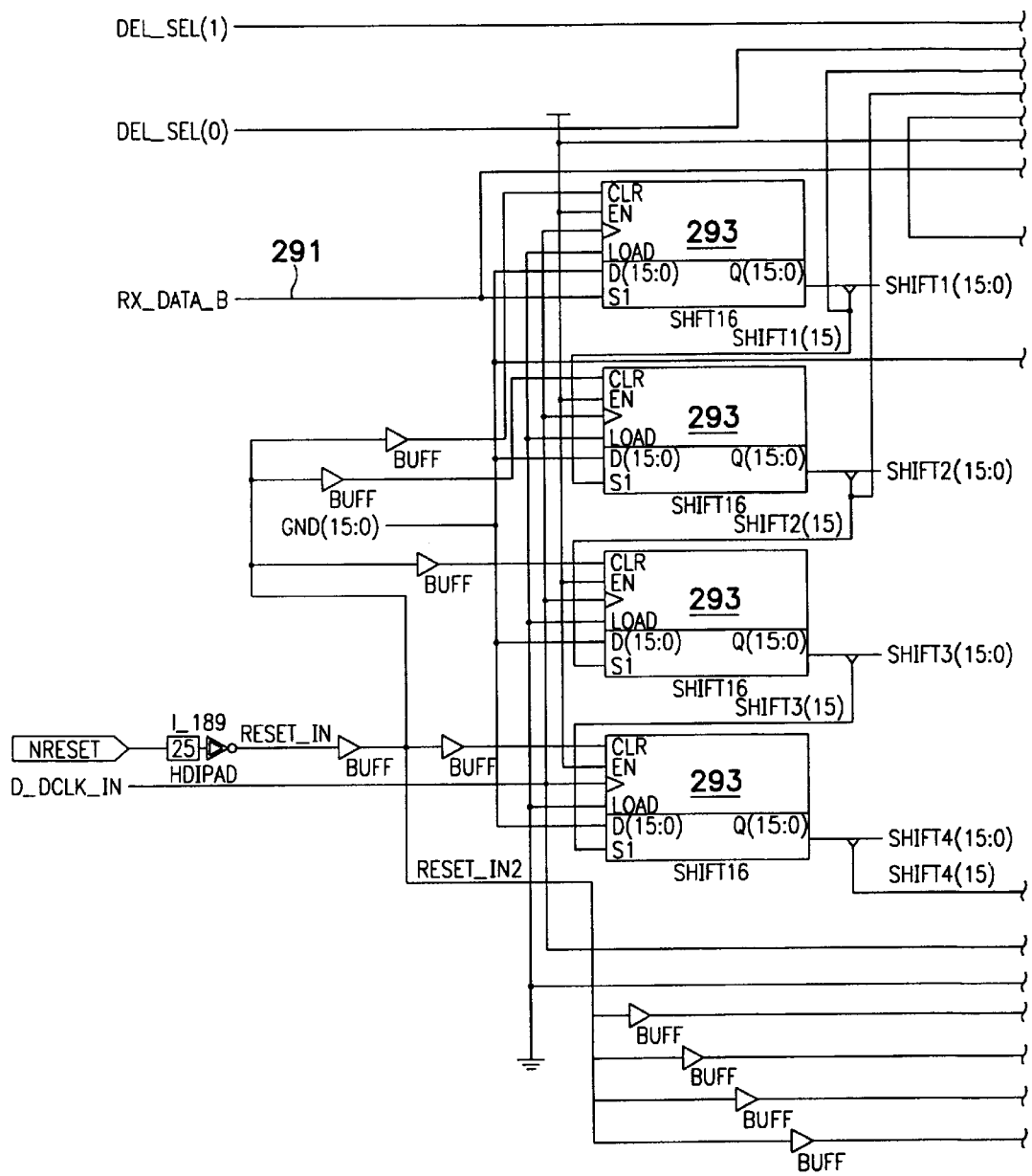
FIG. 7 is a schematic illustration of a digital delay line demodulator in accordance with another embodiment of the present invention.
Figure 7B:
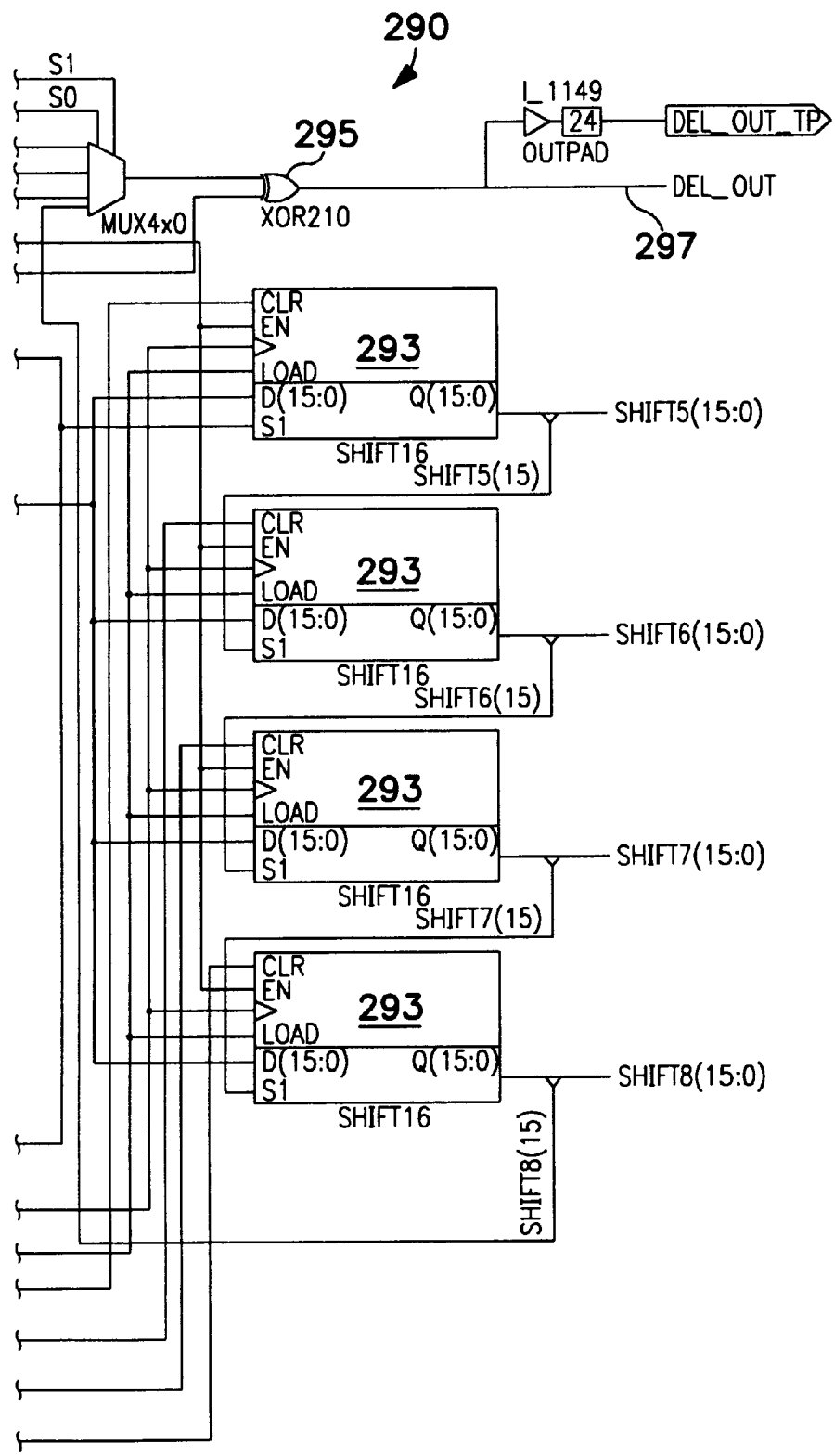

FIG. 7 shows a schematic of a delay line demodulator 290 which is functionally similar to demodulator 270 shown in FIG. 6A. Demodulator 290 illustrated in FIG. 7 includes a number of 16 bit shift registers 293 and an XOR gate 295 to facilitate demodulation of a modulated signal applied to input 291. The demodulated signal produced at the output 297 of demodulator 290 is subsequently processed by a low pass filter, as will be described in greater detail hereinbelow.

Figure 8A:
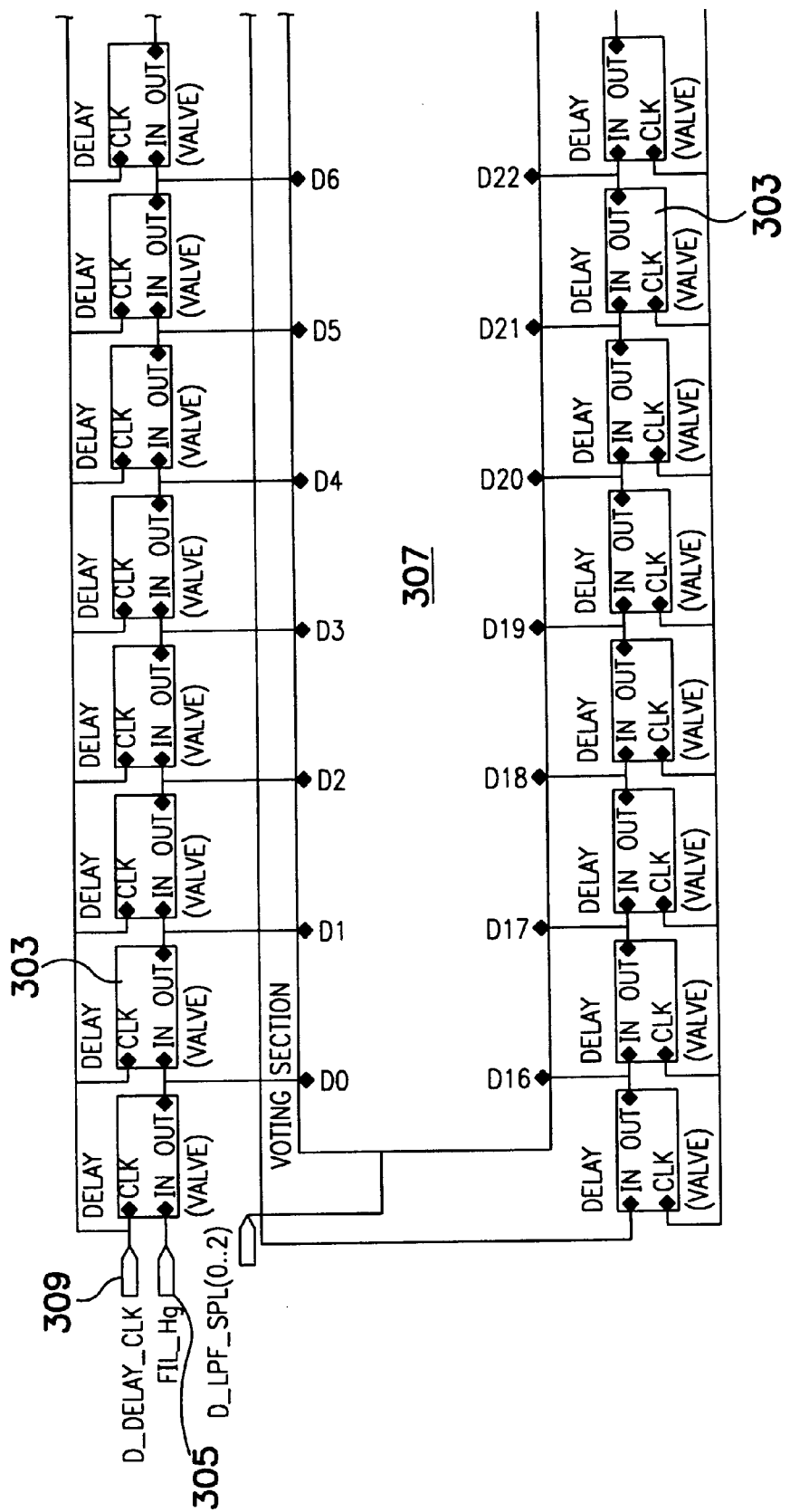
FIG. 8 is a schematic illustration of a digital median filter which employs a majority voting function in accordance with an embodiment of the present invention.
Figure 8B:
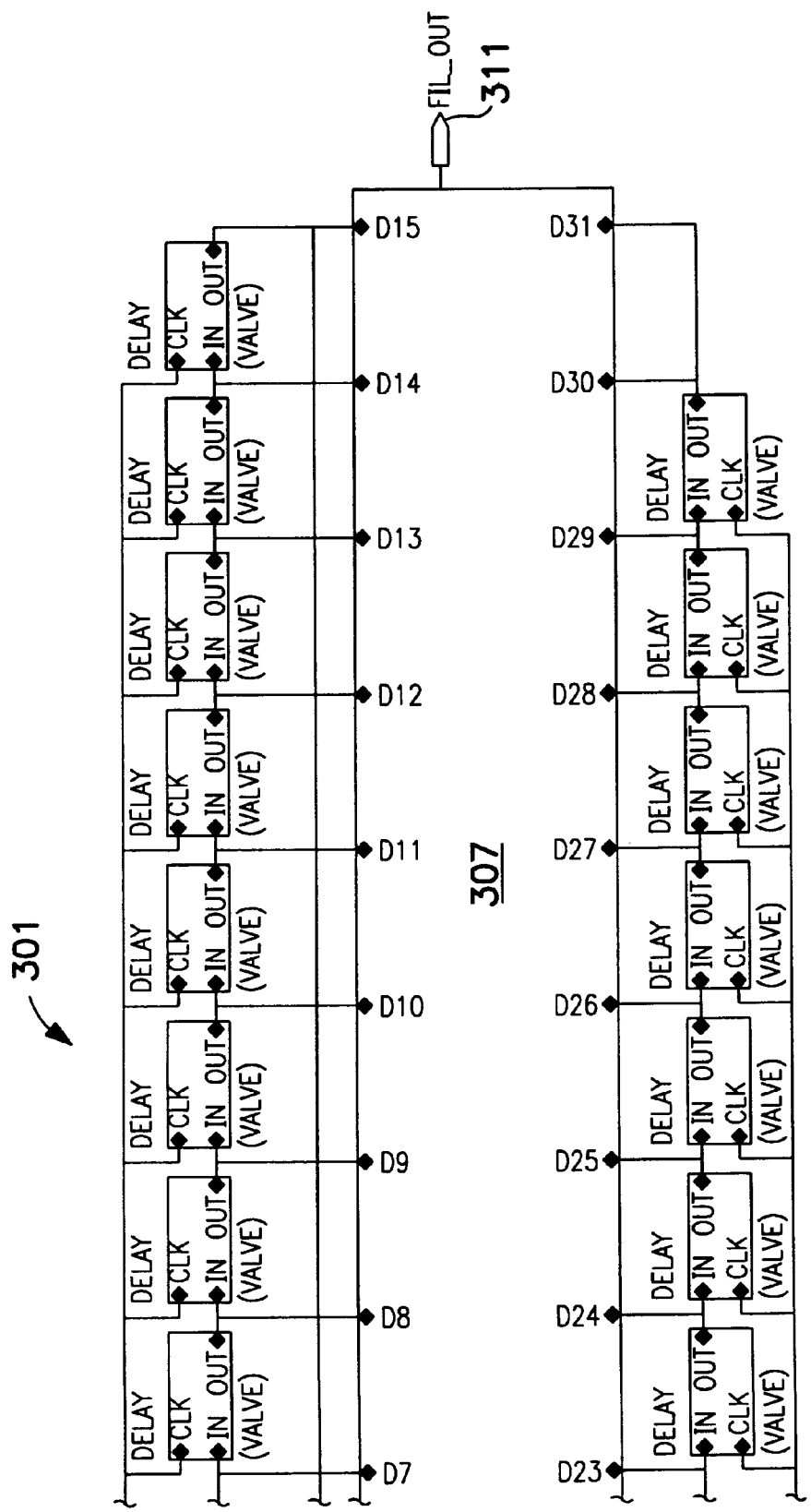

FIG. 8 illustrates an embodiment of a digital filter 301 which processes a demodulated digital IMD signal received from a demodulator, such as digital demodulator of a type previously described. The output signal from a demodulator is processed by digital filter 305 to remove high frequency content which is added to the demodulated signal as a consequence of the demodulation process, as well as from added noise produced within the RF signal channel.

It is to be understood that a digital filter implemented in a manner consistent with the principles of the present invention may receive a demodulated IMD signal from any of a wide variety of demodulation circuits, in addition to those described herein. By way of example, digital filter 301 may receive a digitized demodulated IMD signal produced at the output of a demodulator circuit comprising an analog demodulator and an analog-to-digital converter of a conventional design.

In accordance with the embodiment depicted in FIG. 8, digital filter 301 represents a median filter which operates as a voting filter due to the fact that the input signal has only two states, a high state and a low state. Digital filter 307 generally requires that an odd number of samples, such as 15, 31, or 63 samples for example, be taken during each sampling period. In order to accommodate an even number of samples, a small amount of bias is required in order to indicate whether a sample is more likely to be a zero than a one, and vice versa. The majority of the sequence of sampled data values is determined and represented as a binary signal produced at an output of digital filter 301.

Digital filter 301 includes 31 delay blocks 303, each of which includes a data input which is tied to the data output of an adjacent delay element 303. The clock input of each of the delay blocks 303 is tied to a common clock line 309. The output of each delay element 303 is also coupled to an input of a voting device 307. A detailed description of a digital filter operating in accordance with the principles of the present invention is provided in FIG. 9.

Figure 9:
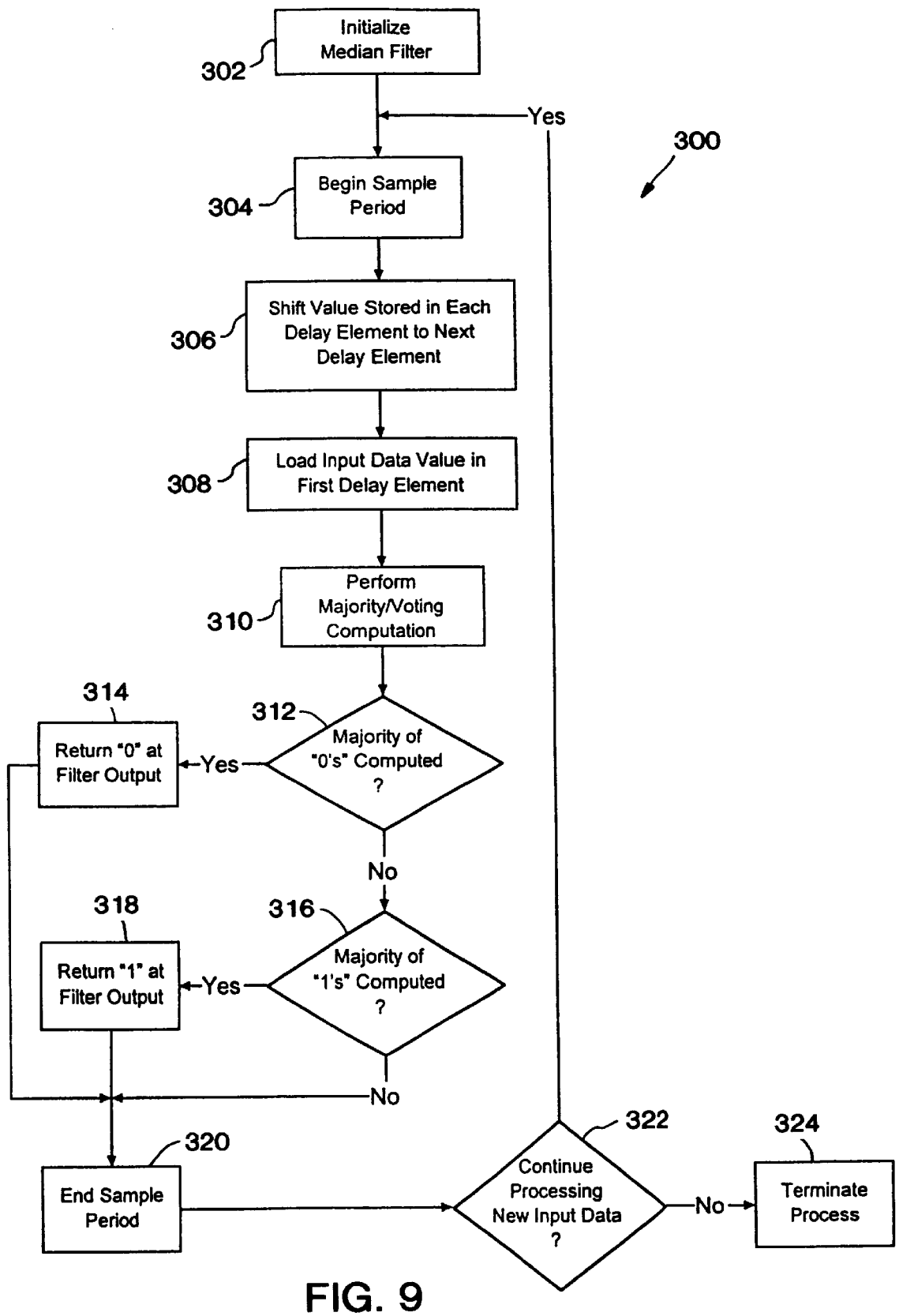
FIG. 9 shows a flow diagram of various process steps performed by a digital median filter implemented in accordance with the principles of the present invention.

FIG. 9 illustrates various process steps performed by a digital filter in accordance with the present invention. Upon initiating the filtering process 300, the digital filter is initialized 302. Initializing the digital filter may be accomplished by setting all delay element output values to 0, and setting the register that holds the voting procedure result to 0. At the beginning of a sample period 304, the values stored in each of the delay blocks are shifted 306 to the next delay element. As a result, the value stored in the last delay element adjacent to the output of the digital filter is lost. A new input data value is loaded 308 into the first delay element adjacent the input of the digital filter.

The process of shifting data values through each of the delay blocks progressively from the digital filter input toward the output of the digital filter effectively provides for a smoothing/windowing functionality. After loading the input data value in the first delay element, a majority/voting computation is performed 310. If the majority of the data values provided at the output of each of the delay blocks are 0's, then a 0 or low value is returned 312, 314 at the output of the digital filter. If the majority of delay element data values are 1's, then a 1 or high value is returned 316, 318 at the digital filter output.

It will be appreciated that various approaches may be employed to perform the majority/voting computation. By way of example, and as a consequence of processing only two symbol types for each sample (i.e., a high and a low symbol), a value of +1 may be assigned to a high symbol or state and a value of −1 may be assigned to a low symbol or state. Determining the state of the majority of latched data values may be accomplished by adding up the sampled data values. If the computed value is positive, a high output value is produced. If the computed value is negative, a low output value is produced.

In accordance with another majority/voting computation approach, only the input and output of the digital filter need be monitored. In accordance with this approach, the value of the incoming bit and the value of the outgoing bit is monitored. A register of the digital filter, such as a multiple-stage shift register, having a fixed number of storage locations, such as 37 storage locations, receives bits at its input in a sequential manner. A counter coupled to the register is used to indicate the majority computation result based on the values of the bits entering and exiting the register.

If the value of the entering bit is a 0 and the value of the exiting bit is a 1, then the counter decrements, thus indicating that the majority of bits currently stored in the register are zero's. If the values of the entering and exiting bits are 1 and 0, respectively, then the counter increments, thus indicating that the majority of bits currently stored in the register are one's. If the value of the entering bit is a 0 and the value of the exiting bit is a 0, then the state of the counter remains unchanged, thus indicating that the majority of bits currently stored is the same as that computed during the previous majority computation.

The majority/voting computation process terminates at the end of the sample period 320. If additional input data values are to be processed 322, the above-described processing steps 304–320 are repeated for each sample period, until such time as the digital filtering process is terminated 324.

Figure 10:
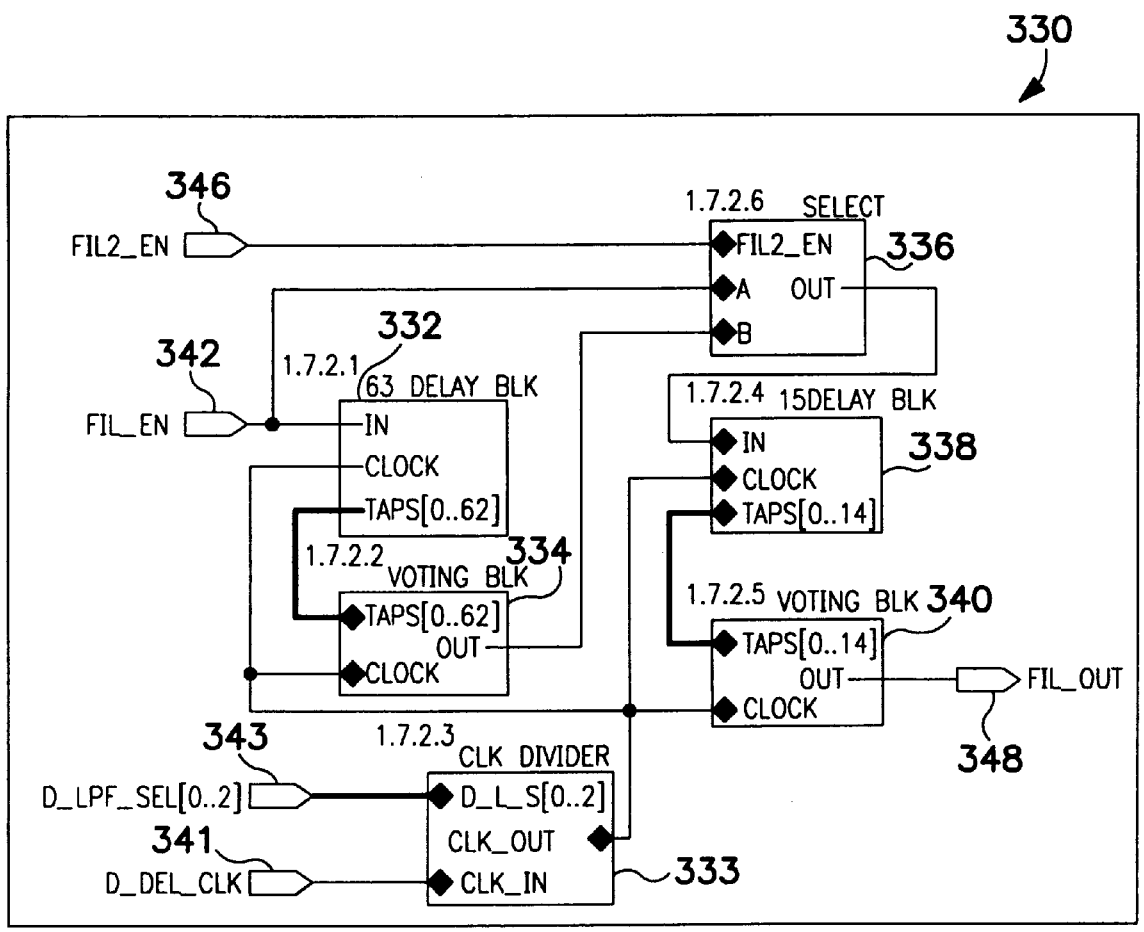
FIG. 10 shows a block diagram of a digital median filter in accordance with another embodiment of the present invention.
Figure 11A:
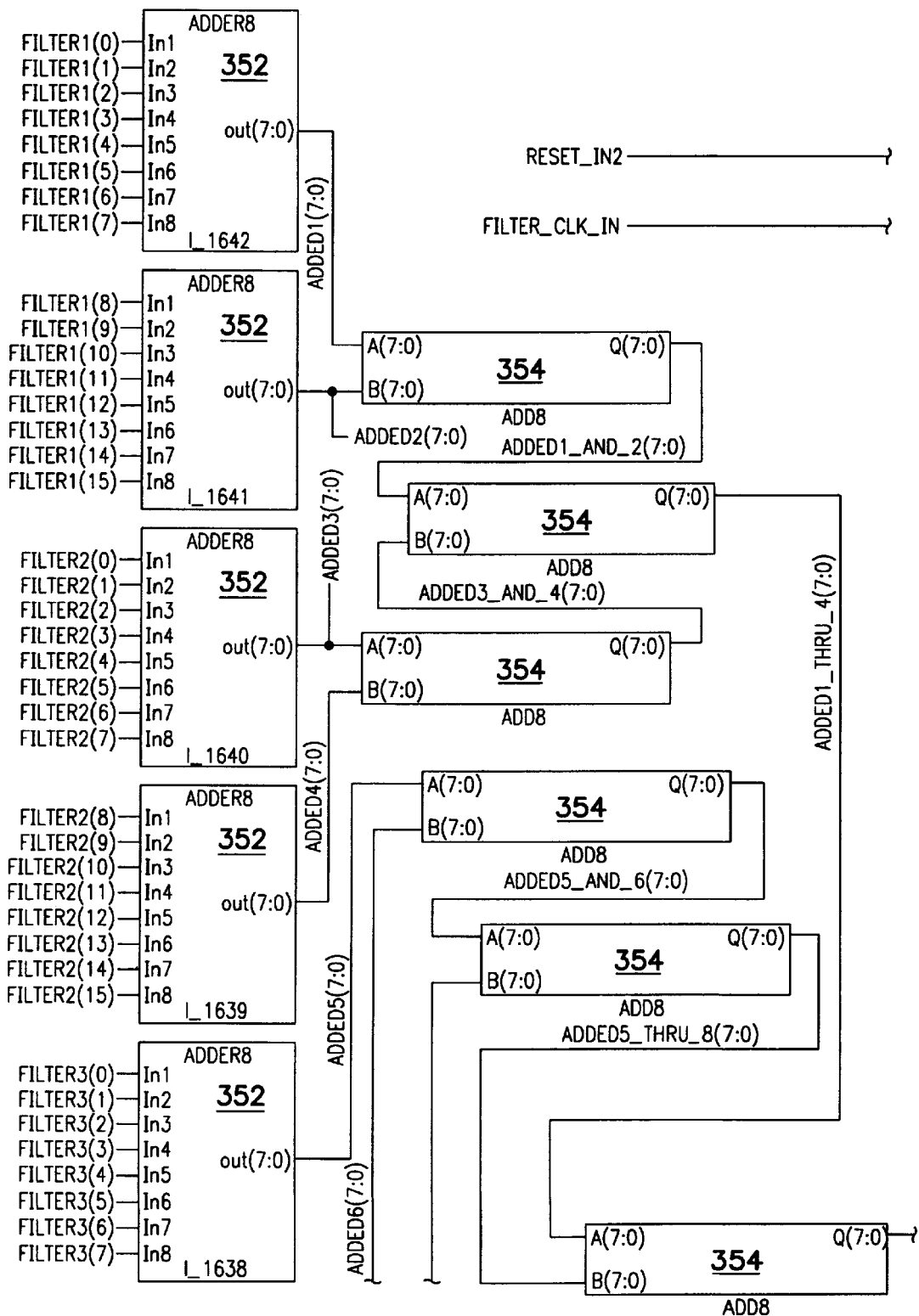
FIG. 11 shows a schematic diagram of a digital median filter in accordance with an embodiment of the present invention.
Figure 11B:
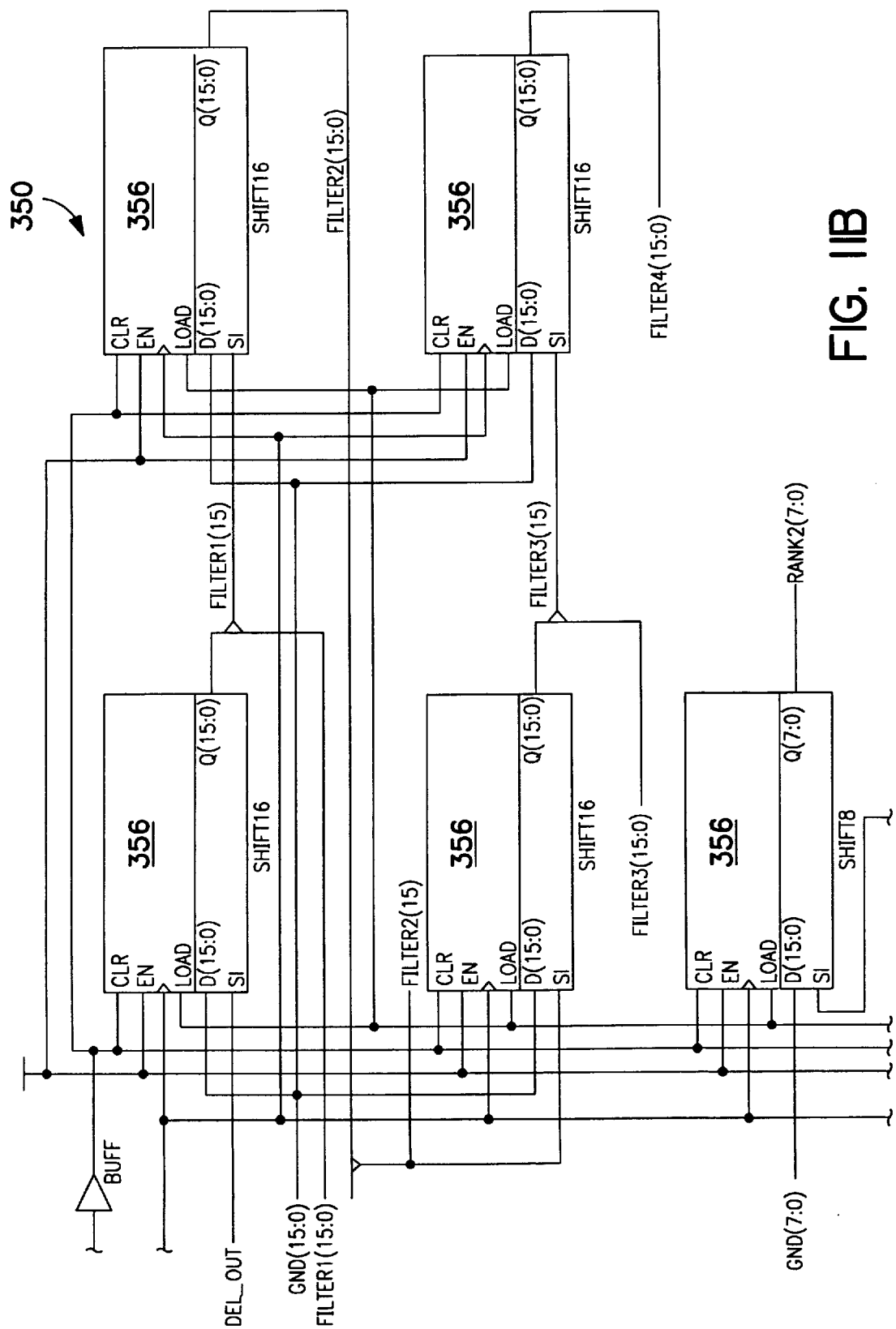
Figure 11C:
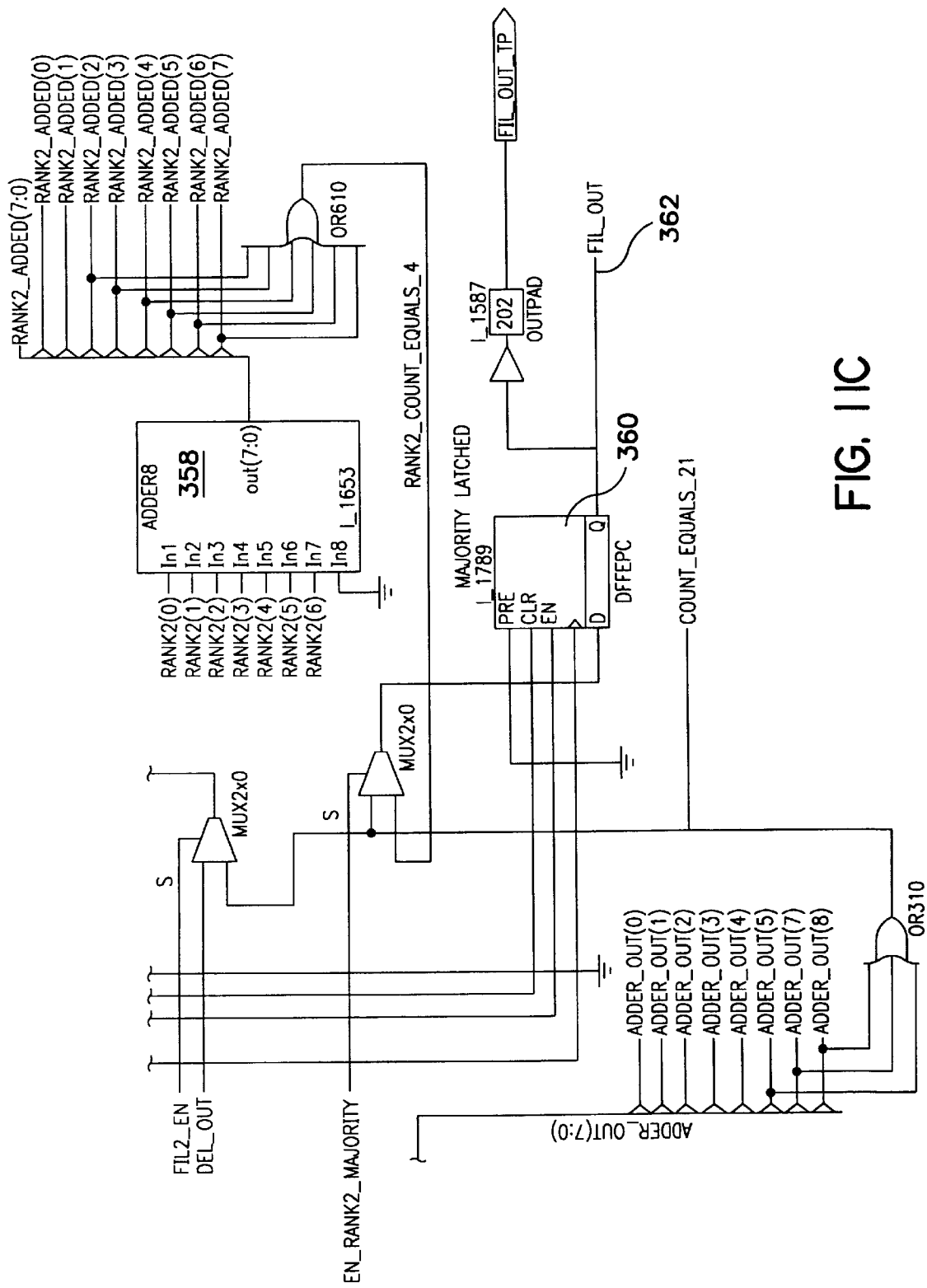
Figure 11D:
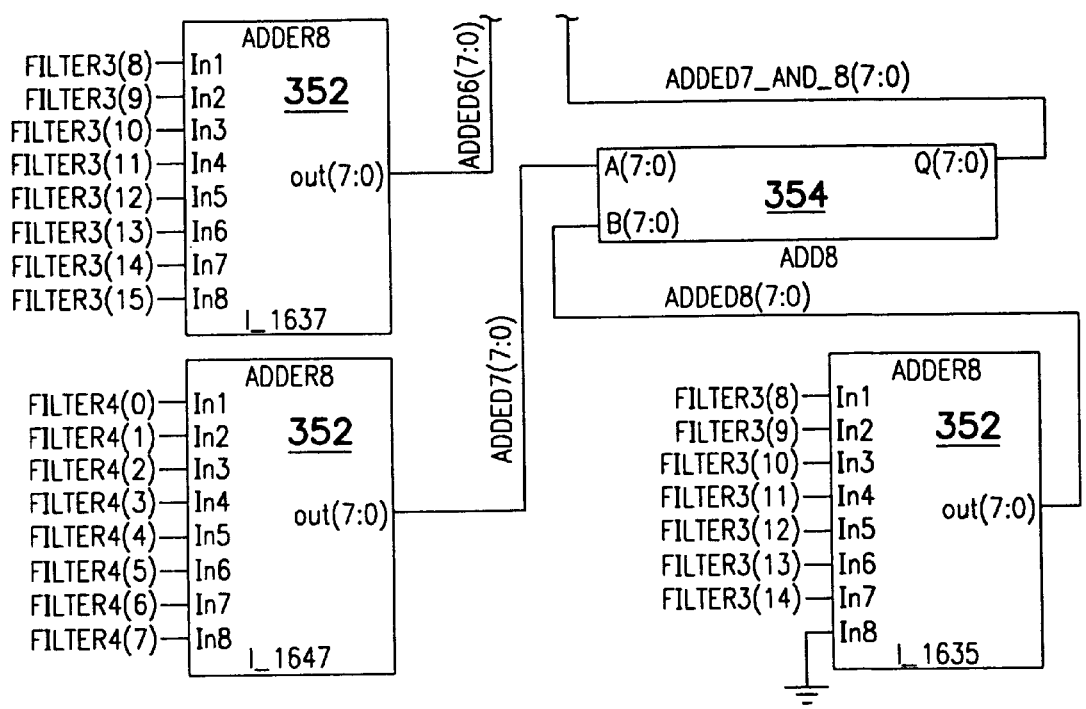

FIG. 10 shows a block diagram of a digital filter in accordance with another embodiment of the present invention. In this embodiment, digital filter 330 includes a number of components including a 63-stage delay line with 63 taps. A voting block 334 performs the above-described majority/voting computation.

Digital filter 330 of FIG. 10 further includes a clock divider 333 which provides for selection of the sample clock frequency. Clock divider 333 provides for selection of a number of different sample frequencies, which provides for the selection of a number of different data rates. Digital filtering is provided by a parallel voting scheme in which each of the previous 63 samples is voted on to determine if there were more 1's than 0's. The voting process preferably occurs at an over-sampled rate, such as an over-sampled rate of 128 times the data rate (e.g., 87.5 Kbps).

Signal 343, identified as D_LPF_SEL[0 . . . 2], may be generated by a user for purposes of changing the low pass filter characteristics of digital filter 330 and/or for changing the data rate by selecting an appropriate sample clock rate. Depending on various operational factors, such as the type of noise present and data throughput requirements, the user has the ability of adjusting the low pass filter to provide for the best overall response and/or data rate. Signal 341, identified as signal D_DEL_CLK, allows for adjusting the digital delay line clock to be divided down so as to provide the desired sample frequency used to clock in the data signal. In one embodiment, the delay line master clock frequency is 11.2 MHz.

In accordance with the digital filter configuration shown in FIG. 10, a select block 336 is provided between the 63-stage filter 332 and a second stage filter 338. Second stage filter 338 is a 15-stage filter which may be selectively activated to provide for additional low pass filtering to remove high frequency noise at the edge or edges of a data bit transition. The select block 336 may be selectively activated or bypassed in response to a select signal 346, identified as signal FIL2_EN. The signal 342, identified as signal FIL_IN, represents the filter input signal which is the digital output signal received from a demodulator. Signal 348, identified as signal FIL_OUT, represents the binary bit stream signal produced at the output of the digital filter 330.

FIG. 11 shows a schematic of a digital filter 350 in accordance with another embodiment of the present invention. In accordance with this embodiment, digital filter 350 includes a number of adder devices 352, 354. As shown, adder devices 352 are 8-bit wide binary input adders, and adder devices 354 are 8-bit wide binary output adders. Digital filter 350 further includes a number of shift registers 356, an adder 358, and a D flip-flop 360 that holds the value of the majority computation result which is provided at the output 362 of digital filter 350.

FIGS. 12–17 show various waveforms produced through computer simulation at they would appear at various points within the demodulation and filtering circuitry of the present invention, and within an implantable medical device. For purposes of illustration, the locations at which the various waveforms illustrated in FIGS. 12–17 are generated will be described with reference to the components shown in FIGS. 3–5.

Figure 12:
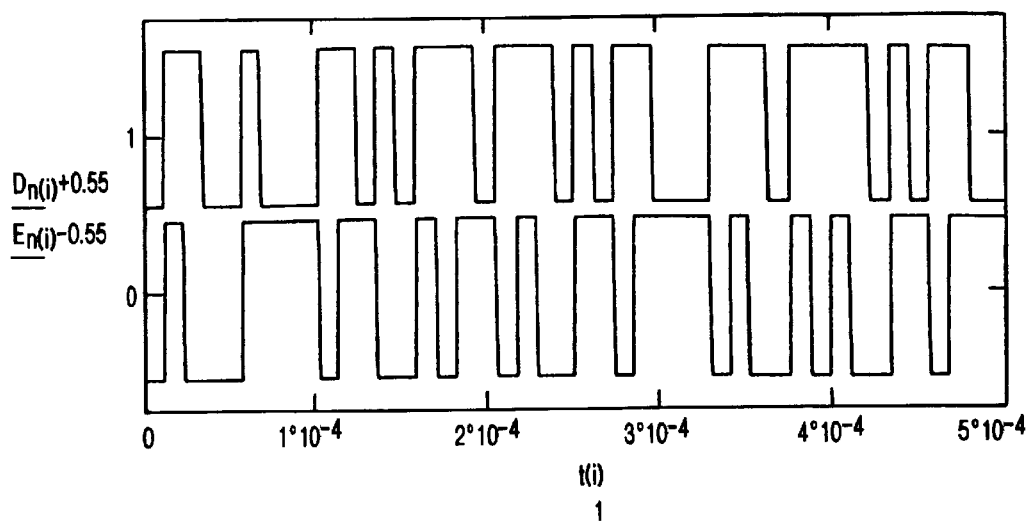
FIG. 12 shows signal waveforms associated with raw and encoded data generated by an implantable medical device in accordance with an embodiment of the present invention.

The waveforms illustrated in FIG. 12, $D_{n(i)}$ and $E_{n(i)}$, represent raw data bits and encoded data produced within IMD 201, respectively. The encoded data signal, $E_{n(i)}$, is produced using the raw data bit stream, $D_{n(i)}$, with modulo-2 addition of a previous bit. The encoded data signal, $E_{n(i)}$, may be characterized by the following equation:

$$E_{n(i)} = \mathrm{mod}[D_{(i)} + E_{(n(i)-1)}, 2] \qquad [1]$$

where, $E_{n(i)}$ represents encoded data produced by using modulo-2 addition of the previous bit and $D_{n(i)}$ represents unencoded data bits. It is noted that the encoded data signal, $E_{n(i)}$, represents the signal provided at the output 210 of encoder 204 of IMD 201.

Modulator 212 impresses the encoded IMD data signal, $E_{n(i)}$, onto a carrier signal having a center frequency of $f_c$ to produce a modulated IMD data signal, $S_i$, as characterized by the following equation:

$$S_i = (2E_{n(i)} - 1) \cdot \cos(2\pi f_c t(i)) \qquad [2]$$

Figure 13:
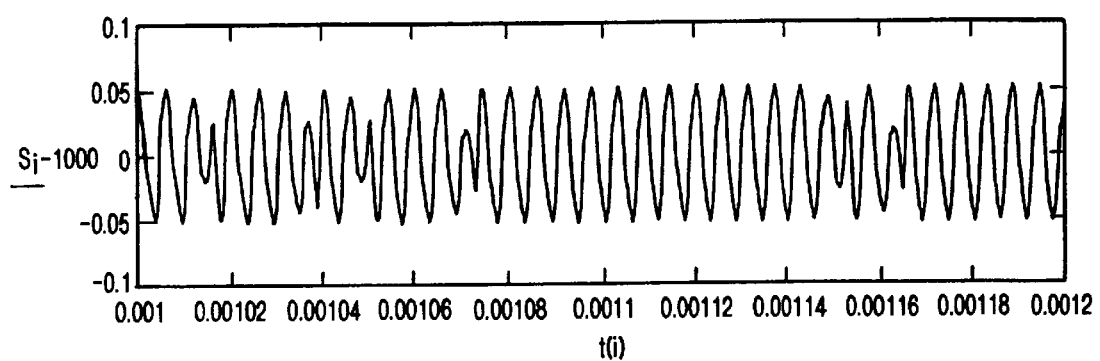
FIG. 13 shows a modulated signal corresponding to the digital encoded waveform shown in FIG. 12 as the modulated signal propagates from the exterior housing of the implantable medical device.

FIG. 13 shows a waveform that represents the modulated signal produced by IMD 201 using the encoded signal, $E_{n(i)}$, illustrated in FIG. 12. The modulated signal shown in FIG. 13 represents the IMD data signal 220 as it leaves a wall of the can 216 which houses IMD 201.

Figure 14:
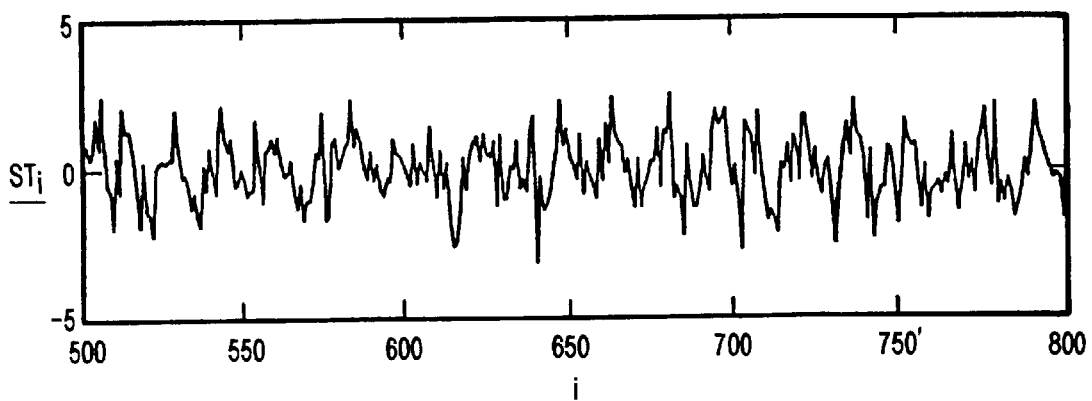
FIG. 14 shows a degraded waveform of that illustrated in FIG. 13 due to noise and other losses associated with body tissue and air media propagation factors.

FIG. 14 shows a corrupted version of the modulated signal shown in FIG. 13 due to noise as the modulated signal propagates through body tissue and air media. Signal $ST_i$ represents the modulated IMD data signal, $S_i$, with noise added to signal, $S_i$.

Figure 15:
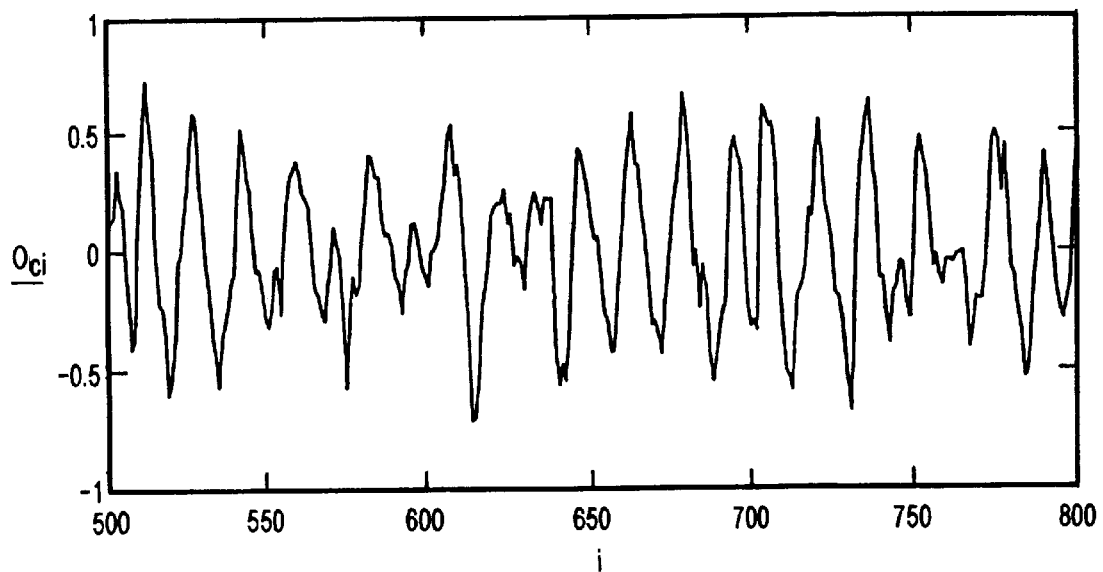
FIG. 15 shows an amplified version of the signal shown in FIG. 14.

FIG. 15 shows an amplified modulated IMD data signal, $O_{ci}$, produced at the output of amplifier 224 of receiver 202 shown in FIG. 3. The digitized modulated IMD data signal, $OI_i$, produced at the output of comparator 226 is given by:

$$OI_i = \begin{cases} 1 & \text{if } O_{ci} > 0 \\ (0) & \text{otherwise} \end{cases} \qquad [3]$$

The delayed digitized modulated IMD data signal, $O\tau d_i$, produced at the outDUtof digital delay line 248 shown in FIGS. 4 and 5, is given by:

$$O\tau d_i = \begin{cases} 0 & \text{if } i < \dfrac{PtsPerBit}{1} \\ OI_{i-\mathrm{ceil}\left(\frac{PtsPerBit}{2}\right)} & \text{otherwise} \end{cases} \qquad [4]$$

where, PtsPerBit represents the number of time points in each data bit, which in the instant simulation is given as 32.

The digitized modulated IMD data signal, $OI_i$, is transmitted to a first input of an exclusive OR gate, such as XOR gate 250 shown in FIGS. 4 and 5, via conductor 252. The delayed digitized modulated IMD data signal, $O\tau d_i$, is transmitted to a second input of XOR gate 250. XOR gate 250 produces a demodulated digital IMD information signal, $Od_i$, at its output, which is characterized by the following equation:

$$Od_i = 2 \cdot \mathrm{mod}\,(OI_i + O\tau d_i, 2) - 1 \qquad [5]$$

Figure 16:
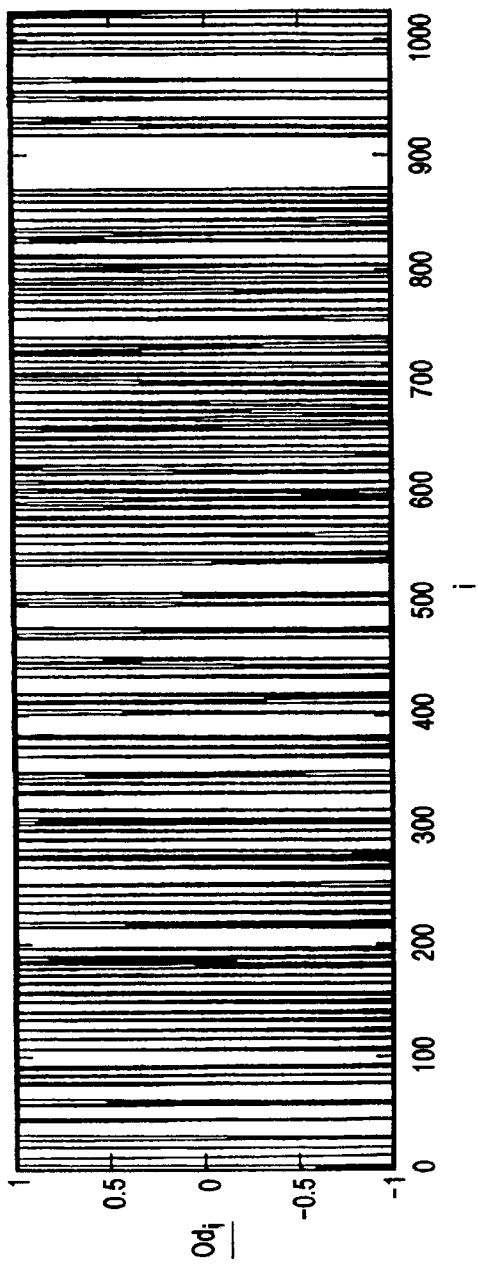
FIG. 16 shows a digitized version of the waveform shown in FIG. 15 subsequent to digital demodulation and prior to processing by a digital filter in accordance with the principles of the present invention.
Figure 17:
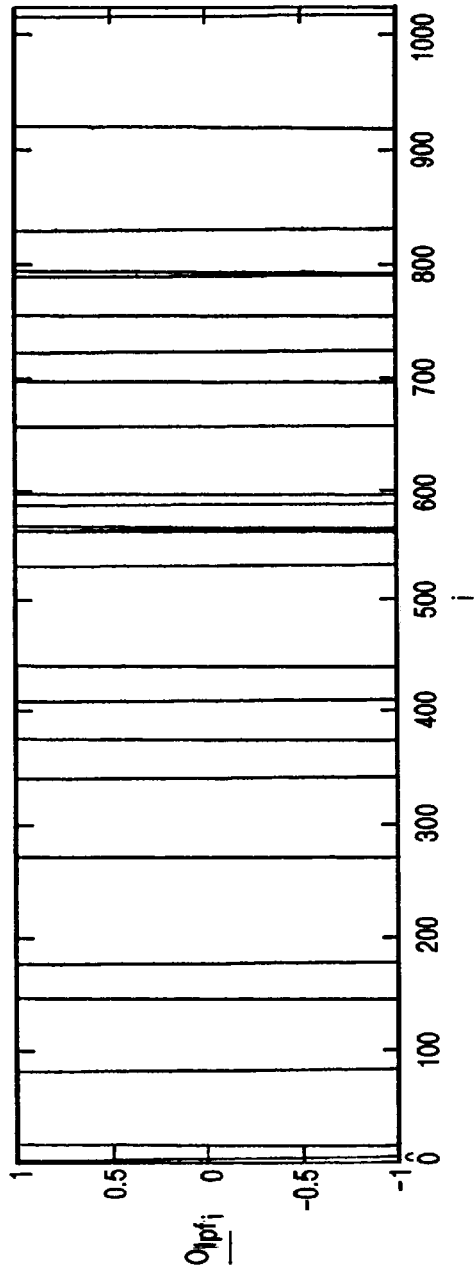
FIG. 17 shows a significantly improved version of the waveform illustrated in FIG. 16 following processing by a digital median filter in accordance with the principles of the present invention.

FIG. 16 shows a waveform which represents a demodulated limited binary signal produced at the output of digital delay line demodulator 230 shown in FIG. 3. Finally, the waveform shown in FIG. 17 depicts a filtered version of the waveform illustrated in FIG. 16 subsequent to processing by low pass digital filter 232, 264 shown in FIGS. 3 and 5, respectively. It will be apparent to those skilled in the art that low pass digital filter 232, 264 provides for the production of a digital representation of analog IMD data which is substantially free of undesirable high frequency noise resulting from channel induced noise, carrier frequency error, data rate inaccuracy, and noise resulting from the demodulation process. Digital filtering in accordance with the principles of the present invention advantageously reduces this unwanted noise, but does not add any significant inner-symbol interference as a result of the filtering process.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to use of a digital delay line receiver in conjunction with a particular implantable medical device, such as a pacemaker, but may be used in conjunction with other medical devices and external receiver/monitoring systems as well. The present invention is also not limited to specific data acquisition and communications techniques, such as those presented herein, but such functions may be directed using other like techniques. The present invention further includes within its scope methods of using the digital delay line receiver, as well as the structural particulars described hereinabove.

What is claimed is:

1. A receiver for a modulated analog telemetry signal transmitted from a body implantable medical device, comprising:
   an antenna;
   an amplifier directly coupled to the antenna to provide an unfiltered signal representative of the modulated analog telemetry signal;
   a demodulator circuit coupled to the amplifier, the demodulator circuit demodulating the unfiltered signal to produce a digital information signal; and
   a digital filter, coupled to the demodulator, that removes high frequency content of the digital information signal to produce a filtered digital information signal.

2. The receiver of claim 1, wherein the digital filter comprises a multiple stage delay line coupled to a multiple tap selection device.

3. The receiver of claim 1, wherein the digital filter includes a plurality of delay blocks and a register, each of the delay blocks having an input coupled to an output of the demodulator circuit and an output coupled to the register.

4. The receiver of claim 1, wherein the digital filter comprises a multiple stage delay line and a voting unit, the voting unit producing a first binary output in response to a majority of delay line stages storing a first value, and the voting unit producing a second binary output in response to a majority of delay line stages storing a second value.

5. The receiver of claim 1, wherein the digital filter comprises a digital signal processor.

6. The receiver of claim 1, wherein the digital filter comprises a first block of filtering elements and a second block of filtering elements coupled to the first block of filtering elements, the second block of filtering elements selectably activated or bypassed in response to a selection signal.

7. The receiver of claim 1, wherein the digital filter comprises a first filter block and a second filter block, the first filter block removing the high frequency content of the digital information signal and the second filter block reducing high frequency noise at an edge of a data bit transition of the digital information signal.

8. The receiver of claim 1, wherein the digital filter filters high frequency content of the digital information signal above a data frequency associated with the digital information signal.

9. The receiver of claim 1, further comprising a control circuit coupled to the digital filter, the control circuit providing selection of a rate at which the digital filter operates.

10. The receiver of claim 1, wherein the digital filter includes a plurality of delay blocks and a voting unit, each of the delay blocks including an input coupled to the demodulator circuit, and output coupled to the voting unit, and a clock input coupled to a clock circuit that produces a clock signal, further wherein varying a rate at which the digital filter operates is effected by the clock circuit varying a frequency of the clock signal.

11. The receiver of claim 1, further comprising a control circuit coupled to the digital filter, the control circuit providing adjustment to a frequency response characteristic of the digital filter.

12. The receiver of claim 1, wherein the digital filter includes a plurality of delay blocks and a voting unit, each of the delay blocks including an input coupled to the demodulator circuit, and output coupled to the voting unit, and a clock input coupled to a clock circuit that produces a clock signal, further wherein varying a frequency response characteristic of the digital filter is effected by the clock circuit varying a frequency of the clock signal.

13. The receiver of claim 1, wherein the digital filter is implemented in a Field-Programmable Gate Array (FPGA) or an Application Specific Integrated Circuit (ASIC).

14. The receiver of claim 1, wherein the implantable medical device comprises one of a pacemaker, a pacemaker/cardioverter/defibrillator (PCD), an oxygen sensing device, a nerve stimulator or a muscle stimulator.

15. A method of digitally filtering a demodulated digital data signal corresponding to a data signal produced by a body implantable medical apparatus, comprising:
   sampling a demodulated digital data signal;
   storing binary values corresponding to samples of the demodulated digital data signal;
   determining a binary value representing a majority of the stored binary values; and
   providing a digital output signal corresponding to the majority binary value.

16. The method of claim 15, wherein determining the binary value representing the majority of the stored binary values comprises determining a binary value corresponding to a most recently obtained demodulated digital data signal and a binary value corresponding to a binary value stored for a longest duration relative to other binary values.

17. The method of claim 15, wherein digitally filtering the demodulated digital data signal filters high frequency content of the demodulated digital data signal above a data frequency associated with the demodulated digital data signal.

18. The method of claim 15, wherein the determining and providing processes are performed using binary values corresponding to a fixed number of most recently obtained demodulated digital data signal samples.

19. The method of claim 15, wherein storing the binary values comprises:

establishing a fixed number of binary values to be stored;

removing a binary value corresponding to a binary value stored for a longest duration relative to other binary values; and storing a binary values corresponding to a binary value corresponding to a most recent sample of the demodulated digital data signal.

20. The method of claim 19, wherein the removing, storing, determining, and providing processes are respectively performed during each of a plurality of sample periods.

21. The method of claim 15, further comprising adjusting a rate at which digital filtering is performed.

22. The method of claim 15, further comprising adjusting a frequency response characteristic associated with digitally filtering the demodulated digital data signal.

23. The method of claim 15, wherein the digital filtering method is performed within a Field-Programmable Gate Array (FPGA) or an Application Specific Integrated Circuit (ASIC).

24. The method of claim 15, wherein the implantable medical device comprises one of a pacemaker, a pacemaker/cardioverter/defibrillator (PCD), an oxygen sensing device, a nerve stimulator or a muscle stimulator.

25. An apparatus for digitally filtering a demodulated digital data signal corresponding to a data signal produced by a body implantable medical apparatus, comprising:

means for sampling a demodulated digital data signal;

means for storing binary values corresponding to samples of the demodulated digital data signal;

means for determining a binary value representing a majority of the stored binary values; and means for providing a digital output signal corresponding to the majority binary value.

26. The apparatus of claim 25, wherein the determining means further comprises means for determining a binary value corresponding to a most recently obtained demodulated digital data signal and a binary value corresponding to a binary value stored for a longest duration relative to other binary values.

27. The apparatus of claim 25, wherein the digital filtering apparatus filters high frequency content of the demodulated digital data signal above a data frequency associated with the demodulated digital data signal.

28. The apparatus of claim 25, wherein the storing means further comprises:

means for establishing a fixed number of binary values to be stored;

means for removing a binary value corresponding to a binary value stored for a longest duration relative to other binary values; and means for storing a binary values corresponding to a binary value corresponding to a most recent sample of the demodulated digital data signal.

29. The apparatus of claim 25 further comprising means for adjusting a rate at which digital filtering is performed.

30. The apparatus of claim 25, further comprising means for adjusting a frequency response characteristic associated with digitally filtering the demodulated digital data signal.

31. The apparatus of claim 25, wherein the apparatus is implemented in a Field-Programmable Gate Array (FPGA) or an Application Specific Integrated Circuit (ASIC).

32. The apparatus of claim 25, wherein the implantable medical device comprises one of a pacemaker, a pacemaker/cardioverter/defibrillator (PCD), an oxygen sensing device, a nerve stimulator or a muscle stimulator.

* * * * *